(12) United States Patent
Bischof et al.

(10) Patent No.: US 11,505,513 B1
(45) Date of Patent: Nov. 22, 2022

(54) CHROMIUM BICYCLIC PHOSPHINYL AMIDINE COMPLEXES FOR TETRAMERIZATION OF ETHYLENE

(71) Applicant: Chevron Phillips Chemical Company LP, The Woodlands, TX (US)

(72) Inventors: Steven M. Bischof, Humble, TX (US); Orson L. Sydora, Sugar Land, TX (US); Daniel H. Ess, Provo, UT (US); Uriah J. Kilgore, Kennewick, WA (US); Doo-Hyun Kwon, Royersford, PA (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 17/521,505

(22) Filed: Nov. 8, 2021

(51) Int. Cl.
| | |
|---|---|
| *C07C 2/36* | (2006.01) |
| *C07F 11/00* | (2006.01) |
| *B01J 31/24* | (2006.01) |
| *B01J 31/14* | (2006.01) |

(52) U.S. Cl.
CPC .............. *C07C 2/36* (2013.01); *B01J 31/143* (2013.01); *B01J 31/2447* (2013.01); *C07F 11/00* (2013.01); *B01J 2231/20* (2013.01); *C07C 2531/14* (2013.01); *C07C 2531/24* (2013.01)

(58) Field of Classification Search
CPC ... C07C 2/36; C07C 2531/14; C07C 2531/24; B01J 31/143; B01J 31/2447; B01J 2231/20; C07F 11/00
See application file for complete search history.

(56) References Cited

U.S. PATENT DOCUMENTS

| | | |
|---|---|---|
| 3,361,525 A | 1/1968 | De Rycke et al. |
| 4,999,263 A | 3/1991 | Kabata |
| 5,217,703 A | 6/1993 | Goodson |

(Continued)

FOREIGN PATENT DOCUMENTS

| | | |
|---|---|---|
| CN | 1490291 A | 5/2005 |
| DE | 1146892 A | 4/1963 |

(Continued)

OTHER PUBLICATIONS

Agapie, T. et al. "Mechanistic Studies of Olefin and Alkyne Trimerization with Chromium Catalysts: Deuterium Labeling and Studies of Regiochemistry Using a Model Chromacyclopentane Complex." Journal American Chemical Society. 2007, 129, pp. 14281-14295.

(Continued)

*Primary Examiner* — Ali Z Fadhel
(74) *Attorney, Agent, or Firm* — Conley Rose, P.C.

(57) ABSTRACT

The present disclosure relates to a catalyst system comprising i) (a) an $N^2$-phosphinyl bicyclic amidine chromium salt or (b) a chromium salt and an $N^2$-phosphinyl bicyclic amidine and ii) an organoaluminum compound. The present disclosure also relate to a process comprising: a) contacting i) ethylene; ii) a catalyst system comprising (a) an $N^2$-phosphinyl bicyclic amidine chromium salt complex or (b) a chromium salt and an $N^2$-phosphinyl bicyclic amidine; ii) an organoaluminum compound, and iii) optionally an organic reaction medium; and b) forming an oligomer product in a reaction zone.

19 Claims, 1 Drawing Sheet

(56) References Cited

U.S. PATENT DOCUMENTS

| | | |
|---|---|---|
| 5,376,742 A | 12/1994 | Krause |
| 5,462,351 A | 10/1995 | Royal |
| 6,046,211 A | 4/2000 | Hansen, Jr. et al. |
| 7,276,566 B2 | 10/2007 | Muruganandam et al. |
| 7,300,904 B2 | 11/2007 | Dixon |
| 7,361,623 B2 | 4/2008 | Dixon |
| 7,554,001 B2 | 6/2009 | Dixon |
| 7,994,363 B2 | 8/2011 | Gao |
| 8,252,956 B2 | 8/2012 | Gao |
| 8,283,555 B2 | 10/2012 | Kokotov et al. |
| 8,367,786 B2 | 2/2013 | Dixon et al. |
| 8,680,003 B2 | 3/2014 | Sydora |
| 8,865,610 B2 | 10/2014 | Sydora |
| 9,283,555 B2 | 3/2016 | Sydora et al. |
| 9,732,106 B2 | 8/2017 | Sydora et al. |
| 10,144,752 B2 | 12/2018 | Sydora et al. |
| 10,183,960 B1 | 1/2019 | Bischof |
| 10,196,328 B2 | 2/2019 | Kilgore |
| 10,232,339 B2 | 3/2019 | Bischof et al. |
| 10,294,171 B2 | 5/2019 | Bischof |
| 10,329,212 B2 | 6/2019 | Fern et al. |
| 10,414,698 B2 | 9/2019 | Fern et al. |
| 10,414,699 B2 | 9/2019 | Bischof et al. |
| 10,435,336 B2 | 10/2019 | Kreischer |
| 10,464,862 B2 | 11/2019 | Bischof |
| 10,493,442 B2 | 12/2019 | Bischof |
| 10,807,921 B2 | 10/2020 | Kilgore et al. |
| 11,117,845 B2 | 9/2021 | Kilgore |
| 2002/0182124 A1 | 12/2002 | Woodard et al. |
| 2006/0247399 A1 | 11/2006 | McConville et al. |
| 2007/0149582 A1 | 6/2007 | Kordes et al. |
| 2007/0185360 A1 | 8/2007 | Buchanan et al. |
| 2008/0207973 A1 | 8/2008 | Palmas et al. |
| 2010/0041841 A1 | 2/2010 | Terry et al. |
| 2010/0113852 A1* | 5/2010 | Sydora ............... B01J 31/143 585/513 |
| 2010/0222622 A1 | 9/2010 | Overett et al. |
| 2010/0240847 A1 | 9/2010 | Dixon et al. |
| 2010/0274065 A1 | 10/2010 | Sydora |
| 2012/0142989 A1 | 6/2012 | Jaber et al. |
| 2012/0309965 A1 | 12/2012 | Sydora |
| 2013/0090508 A1 | 4/2013 | Wang et al. |
| 2013/0331629 A1 | 12/2013 | Sydora et al. |
| 2016/0375431 A1 | 12/2016 | Carney et al. |
| 2017/0341998 A1 | 11/2017 | Bischof et al. |
| 2017/0341999 A1 | 11/2017 | Fern et al. |
| 2017/0342000 A1 | 11/2017 | Bischof et al. |
| 2017/0342001 A1 | 11/2017 | Fern et al. |
| 2017/0349505 A1* | 12/2017 | Kilgore ............... B01J 31/143 |
| 2019/0263732 A1 | 8/2019 | Kreischer et al. |

FOREIGN PATENT DOCUMENTS

| | | |
|---|---|---|
| EP | 0780353 A1 | 6/1997 |
| EP | 1414879 A1 | 5/2004 |
| EP | 2684857 A1 | 1/2014 |
| EP | 2344548 B1 | 12/2014 |
| WO | 2002004119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011082192 A1 | 7/2011 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2013184579 A1 | 12/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |
| WO | 2017078843 A1 | 5/2017 |
| WO | 2017209959 A1 | 12/2017 |

OTHER PUBLICATIONS

Beh, E., et al. "Synthesis of 5,5-Bicyclic Amidines as Ligands for Thermally Stable Vapor Deposition Precursors." Organometallics. 2017, 36, pp. 1453-1456.

Bollmann, A. et al., "Ethylene tetramerization: a new route to produce 1-octene in exceptionally high selectivities." Journal American Chemical Society. 2004, 126, pp. 14712-14713.

Buchelli, et al., "Determination of Polyolefin Powder Flow Characteristic in a Purge Column During Transitions," Ind. Eng. Chem. Res., 2007, vol. 46, No. 24, pp. 8120-8129.

Carter, A., et al. "High Activity Ethylene Trimerisation Catalysts based on Diphoshine Ligands." Chemical Communications. Mar. 20, 2002. pp. 858-859.

Sydora, O. et al. "Selective Ethylene Tri-/Tetramerization Catalysts." ACS Catalysts. 2012, 2, pp. 2452-2455.

AkzoNobel Product Data Sheet MMAO-20/Heptane Solutions, 2014, 2 pgs.

AkzoNobel Product Data Sheet MMAO-3A/Heptane Solutions, 2014, 2 pgs.

AkzoNobel Safety Data Sheet MMAO-20 11-30% in Heptane, 2007, 9 pgs.

AkzoNobel Safety Data Sheet MMAO-3A 7 wt % Al in Heptane, 2016, 17 pgs.

Bartlett, Stuart A., et al., "Activation of [CrCl3{R-SN(H)S-R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.

Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.

Braunstein, Pierre, et. al. "Synthesis of Nickel Phenyl Complexes with New Chelating κ2-P,N Ligands Derived from α-Iminoazatriphenylphosphoranes," Journal of Organometallic Chemistry, 1999, vol. 582, pp. 371-377, Elsevier Science S.A.

Braunstein, Pierre, et. al. "Synthesis of Nickel Phenyl Complexes with New Chelating κ2-P,N Ligands Derived from α-Iminoazatriphenylphosphoranes. [Erratum to document cited in CA127:17791]," Journal of Organometallic Chemistry, 1999, vol. 582, p. 370, Elsevier Science S.A.

Braunstein, Pierre, et. al., "Synthesis of Nickel Phenyl Complexes with New Chelating κ2-P,N Ligands Derived from α-Iminoazatriphenylphosphoranes," Journal of Organometallic Chemistry, 1997, vol. 529, pp. 387-393, Elsevier Science S.A.

Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.

Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of Chemistry.

Buckley, G. D., et al., "Aliphatic Nitro-compounds. Part XV. Preparation of Heterocyclic Bases by Reduction of 3-Nitroalkyl Cyanides," 1947, pp. 1508-1511, Imperial Chemical Industries Limited, Research Laboratories, United Kingdom.

(56) References Cited

OTHER PUBLICATIONS

Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.

Dyer, Philip W., et al., "Rigid N-Phosphino Guanidine P,N Ligands and Their Use in Nickel-Catalyzed Ethylene Oligomerization," Organometallics, 2008, vol. 27, pp. 5082-5087, American Chemical Society.

Fawcett, F.S., et al., "Cyanogen Fluoride: Synthesis and Properties," Journal of the American Chemical Society, Jul. 5, 1964, pp. 2576-2579, vol. 86, No. 13, American Chemical Society.

Foreign communication from a related counterpart application—International Search Report and Written Opinion, PCT/US2017/032191, dated Aug. 14, 2017, 15 pages.

Foreign communication from a related counterpart application—International Search Report and Written Opinion, PCT/US2017/032199, dated Aug. 17, 2017, 14 pages.

Foreign communication from a related counterpart application—International Search Report and Written Opinion, PCT/US2017/033162, dated Jun. 30, 2017, 10 pages.

Foreign communication from a related counterpart application—International Search Report and Written Opinion, PCT/US2017/033165, dated Aug. 3, 2017, 11 pages.

Foreign communication from a related counterpart application—International Search Report and Written Opinion, PCT/US2017/033168, dated Aug. 3, 2017, 8 pages.

Gong, D., et al., "Ethylene polymerization by PN3-type pincer chromium(III) complexes," Journal of Molecular Catalysis A: Chemical, 2014, pp. 100-107, vol. 395, Elsevier B. V.

Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.

Group notation revised in periodic table, Feb. 4, 1985, C&EN, pp. 26-27.

Hossain, Anwar, et al., "Spin-crossover in Chromium-catalyzed Ethylene Trimerization" Density Functional Theory Study,"Bulletin of the Korean Chemical Society, Sep. 2014," pp. 2835-2838, vol. 35, No. 9, Korea Chemical Society.

Imhoff, Donald W., et al., "Characterization of Methylaluminoxanes and Determination of Trimethylaluminum Using Proton NMR," Organometallics, 1998, pp. 1941-1945, vol. 17, American Chemical Society.

Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186.

Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.

Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.

Mcguinness, D. S., et al., "Novel CR-PNP complexes as catalysts for the trimerisation of ethylene," Chemical Communications—CHEMCOM, Jan. 1, 2003, pp. 334-335, The Royal Society of Chemistry.

Mcnaught, Alan D., et al., "Compendium of Chemical Terminology," IUPAC Recommendations, Second edition, 1997, 5 pages, Wiley-Blackwell.

Milton, Heather L., et al., "Investigating the effects of steric hindrance on the coordination of 2-aminothiazoyl based ligands," Inorganica Chimica Acta, 2005, vol. 358, pp. 1393-1400, Elsevier B.V.

Morse, J. G., et al., "Substituted Difluoro- and Dichlorophosphines," Inorganic Syntheses, 1967, pp. 147-156, vol. 10, McGraw-Hill Book Company, Inc.

Office Action dated Aug. 30, 2017 (28 pages), U.S. Appl. No. 15/167,017, filed May 27, 2016.

Office Action (Final) dated Feb. 28, 2018 (43 pages), U.S. Appl. No. 15/167,017, filed May 27, 2016.

Office Action dated Jul. 27, 2018 (24 pages), U.S. Appl. No. 15/167,017, filed May 27, 2016.

Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.

Shankaran, K, et al., "Evaluation of pyrrolidin-2-imines and 1,3-thiazolidin-2-imines as inhibitors of nitric oxide synthase," Bioorganic & Medicinal Chemistry Letters, 2004, pp. 4539-4544, vol. 14, Elsevier Ltd.

Singh, Rajendra P., et al., "The first application of SelectfluorTM in electrophilic fluorination of amines: a new route to —NF2, —NHF, and >NF compounds," Chemical Communication, 2001, pp. 1196-1197, vol. 13, Royal Society of Chemistry.

Van Rensburg, Werner Janse, et al., "A Df I Study toward the Mechanish of Chromium-Catalyzed Ethylene Frimerization," Organometallics, Feb. 17, 2004, pp. 1207-1222, vol. 23, No. 6, American Chemical Society.

Voß, Corinna, et al., Intramolecular d10-d10 interactions in neutral, dinuclear Au(I) complexes supported by amino-thiazoline- and -thiazole-based P,N-phosphine ligands, C.R. Chimie, vol. 15, 2012, pp. 229-236, Elsevier Masson SAS.

Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.

Zhang, Shuanming, et al., "Reactions of a Phosphinoimino-thiazoline-Based Metalloligand with Organic and Inorganic Electrophiles and Metal-Induced Ligand Rearrangements," Organometallics, 2010, vol. 29, pp. 6660-6667, American Chemical Society.

Filing receipt and specification for patent application entitled "Chromium Phosphinyl Isoindole Amidine Complexes for Tetramerization of Ethylene," by Steven M. Bischof, et al., filed Nov. 8, 2021 as U.S. Appl. No. 17/521,494.

Filing receipt and specification for patent application entitled "Chromium Phosphinyl Hydroisoindole Amidine Complexes for Tetramerization of Ethylene," by Steven M. Bischof, et al., filed Nov. 8, 2021 as U.S. Appl. No. 17/521,508.

* cited by examiner

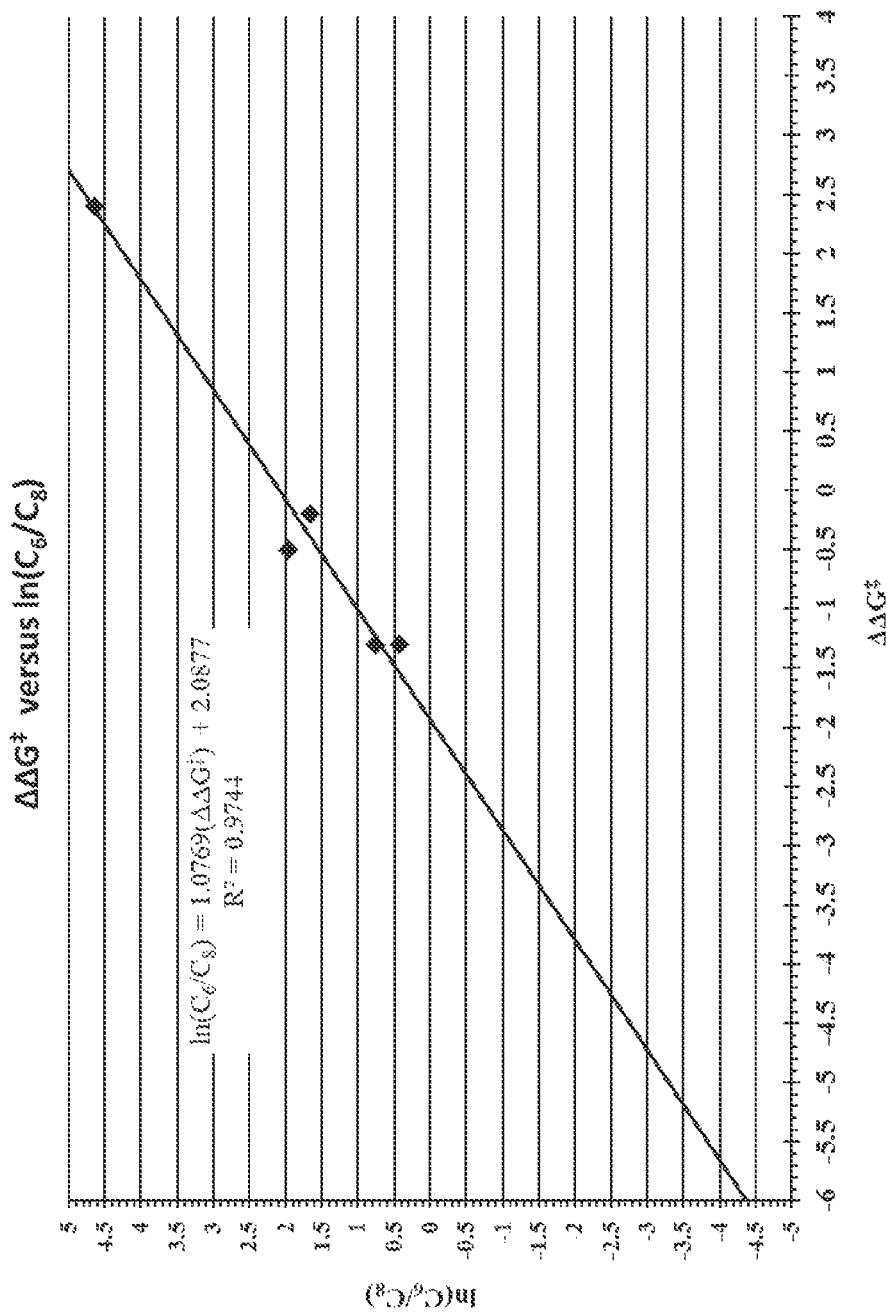

CHROMIUM BICYCLIC PHOSPHINYL AMIDINE COMPLEXES FOR TETRAMERIZATION OF ETHYLENE

TECHNICAL FIELD

This disclosure relates to catalyst systems comprising $N^2$-phosphinyl bicyclic amidine and a chromium salt or a $N^2$-phosphinyl bicyclic amidine chromium salt complex. The disclosure also relates to using the catalyst systems comprising the $N^2$-phosphinyl bicyclic amidine and a chromium salt or the $N^2$-phosphinyl bicyclic amidine chromium salt complex in the oligomerization of ethylene.

BACKGROUND

Olefins, also commonly known as alkenes, are important items of commerce. Their many applications include employment as intermediates in the manufacture of detergents, as precursors to more environmentally friendly refined oils, as monomers, and as precursors for many other types of products. An important subset of olefins is alpha olefins. One method of making alpha olefins is via oligomerization of ethylene, which is a catalytic reaction involving various types of catalysts and/or catalyst systems. Examples of catalysts and catalyst systems used commercially in the oligomerization of ethylene include alkylaluminum compounds, certain nickel-phosphine complexes, a titanium halide with a Lewis acid (e.g., diethyl aluminum chloride), a selective 1-hexene catalyst system containing a chromium containing compound (e.g., a chromium carboxylate), a nitrogen containing ligand (e.g., a pyrrole), a metal alkyl (e.g., alkyl aluminum compounds), and selective trimerization and/or tetramerization catalyst systems using a metal complex of a compound having a diphosphinylaminyl group.

Several non-commercial ethylene oligomerization catalyst systems are based upon metal complexes of pyridine bis-imines, and metal complexes of α-diimine compounds having a metal complexing group. These catalyst systems typically use an alkyl aluminum compound (e.g., aluminoxane) to activate the metal complexes for olefin oligomerization.

Applications and demand for olefins (e.g., alpha olefins) continue to multiply, and competition to supply them correspondingly intensifies. Thus, additional novel and improved catalyst systems and methods for ethylene oligomerization are desirable.

SUMMARY

Disclosed herein is a catalyst system comprising i) (a) an $N^2$-phosphinyl bicyclic amidine chromium salt complex having Structure NPBACr I or Structure NPBACr II

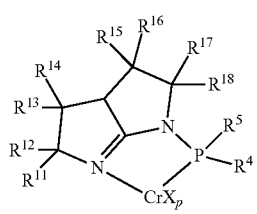

NPBACr I

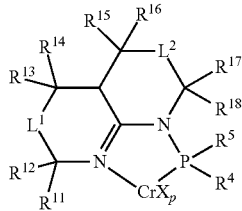

NPBACr II or (b) a chromium salt and an $N^2$-phosphinyl bicyclic amidine having Structure NBPA I or Structure NPBA II

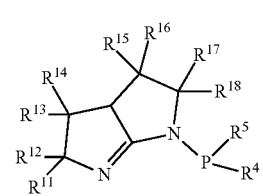

NPBA I

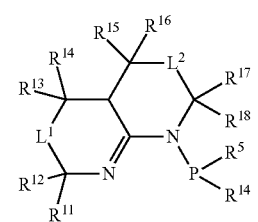

NPBA II wherein $R^{11}$, $R^{12}$, $R^{13}$, $R^{14}$, $R^{15}$, $R^{16}$, $R^{17}$, and $R^{18}$ independently can be a hydrogen or a $C_1$ to $C_{30}$ organyl group, $L^1$ and $L^2$ independently can be a $C_1$ to $C_{30}$ a hydrocarbylene group, $R^4$ and $R^5$ independently can be a $C_1$ to $C_{30}$ organyl group and $R^4$ and $R^5$ optionally can be combined to form $L^{45}$ forming a ring or ring system including the phosphorus atom where $L^{45}$ can be a $C_1$ to $C_{30}$ organylene group, and $CrX_p$ is a chromium salt where X is a monoanion and p is an integer from 2 to 6; and ii) an organoaluminum compound.

Also disclosed herein is a process comprising: a) contacting i) ethylene; ii) a catalyst system comprising (a) (i) an $N^2$-phosphinyl bicyclic amidine chromium salt complex having Structure NPBACr I and/or Structure NPBACr II

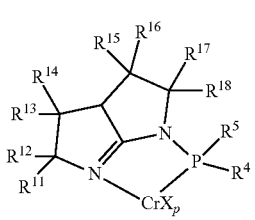

NPBACr I

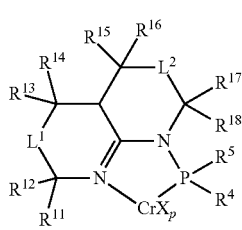

NPBACr II or (ii) a chromium salt and an $N^2$-phosphinyl bicyclic amidine having Structure NPBA I or Structure NPBA II

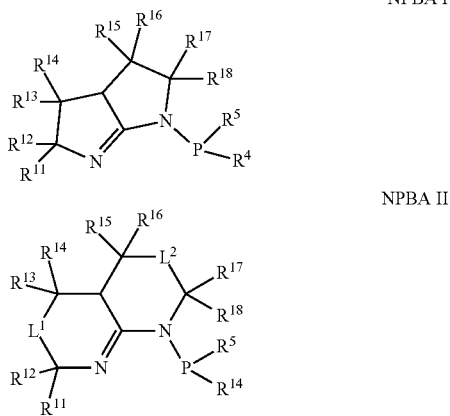

NPBA I

NPBA II wherein $R^{11}$, $R^{12}$, $R^{13}$, $R^{14}$, $R^{15}$, $R^{16}$, $R^{17}$, and $R^{18}$ independently can be a hydrogen or a $C_1$ to $C_{30}$ organyl group, $L^1$ and $L^2$ independently can be a $C_1$ to $C_{30}$ a hydrocarbylene group, $R^4$ and $R^5$ independently can be a $C_1$ to $C_{30}$ organyl group and $R^4$ and $R^5$ optionally can be combined to form $L^{45}$ forming a ring or ring system including the phosphorus atom where $L^{45}$ can be a $C_1$ to $C_{30}$ organylene group, and $CrX_p$ is a chromium salt where X is a monoanion and p is an integer from 2 to 6; (b) an organoaluminum compound, and iii) optionally an organic reaction medium; and b) forming an oligomer product in a reaction zone.

BRIEF DESCRIPTION OF THE DRAWINGS

FIG. 1 is a plot the calculated Gibbs free energy difference, $\Delta\Delta G^‡$, between the transition states leading to 1-hexene and 1-octene versus the natural logarithm of the quantity of 1-hexene and 1-octene ($\ln(C_6/C_8)$) for five experimentally evaluated ethylene oligomerizations using five $N^2$-phosphinylamidine chromium salt complex catalyst systems and the predictive values $\Delta\Delta G^‡$.

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in Chemical and Engineering News, 63(5), 27, 1985. In some instances, a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the subject matter described herein. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms "comprising," "consisting essentially of," and "consisting of" apply only to the feature class which is utilized and it is possible to have different transitional terms or phrases utilized with different features within a claim. For example, a method can comprise several recited steps (and other non-recited steps) but utilize a catalyst system preparation consisting of specific steps; or alternatively, consist of specific steps and/or utilize a catalyst system comprising recited components and other non-recited components.

Within this specification, use of "comprising" or an equivalent expression contemplates the use of the phrase "consisting essentially of," "consists essentially of," or equivalent expressions as alternative aspects to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative aspects for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

An $N^2$-phosphinyl bicyclic amidine refers a amidine compound where the two nitrogen atoms of the $N^2$-phosphinyl amidine group are in separate rings of a bicyclic ring system.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. "Organyl groups," "organylene groups," and "organic groups" can be aliphatic (inclusive of being cyclic or acyclic, or linear or branched) or can be aromatic.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group), from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. endocyclic double or triple bonds, respectively, can be identified by use of the term "mono," "di," "tri," etc. . . . within the name of the cycloalkene or cycloalkyne. Cycloalkenes and cycloalkynes can further identify the position of the endocyclic double or triple bonds.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or ring system. The term "olefin" includes aliphatic and aromatic, acyclic and cyclic, and/or linear and branched compounds having at least one carbon-carbon double bond that is not part of an aromatic ring or ring system unless specifically stated otherwise. Olefins having only one, only two, only three, etc. carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched hydrocarbon olefin that has one or more carbon-carbon double bonds. Alkenes having only one, only two, only three, etc. such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated. The term "linear alpha olefin" as used herein refers to a non-branched alpha olefin having a carbon-carbon double bond between the first and second carbon atom.

The term "normal alpha olefin" whenever used in this specification and claims refers to a linear hydrocarbon mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and additional double bonds.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" which are heteroaromatic compounds formally derived from arenes by replacement of one or more methine (—C═) carbon atoms of the cyclically conjugated double bond system with a trivalent or divalent heteroatom, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group is generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon in the methylene group in diphenylmethane; oxygen in diphenyl ether; nitrogen in triphenyl amine; among other linking groups). As disclosed herein, the term "substituted" can be used to describe an aromatic group, arene, or heteroarene wherein a non-hydrogen moiety formally replaces a hydrogen in the compound and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An "aryl compound" refers to an aromatic hydrocarbon. An "aryl group" refers to univalent aromatic hydrocarbon having a free valance at an aromatic ring carbon atom. Similarly, a "arylene group" refers to a group derived by removing two hydrogen atoms from an aromatic hydrocarbon, at least one of which is an aromatic ring carbon. Thus, an "arylene group" includes both a group derived from an aromatic hydrocarbon in which two hydrogen atoms are formally removed from the same aromatic ring carbon, a group derived from an aromatic hydrocarbon in which two hydrogen atoms are formally removed from two different aromatic ring carbons, and a group derived from an aromatic hydrocarbon in which a first hydrogen atom is formally removed from an aromatic ring carbon and a second hydrogen atom is formally removed from a carbon atom that is not an aromatic ring carbon. An "aromatic hydrocarbon group" refers to a generalized group formed by removing one or more hydrogen atoms (as necessary for the particular group and at least one of which is an aromatic ring carbon) from an aromatic hydrocarbon compound.

An "arylalkane" refers to an aromatic hydrocarbon having at least one alkyl group substituent. An "aralkyl group" is an aryl-substituted alkyl group having a free valance at a non-aromatic carbon atom of an arylalkane (e.g., a benzyl group, or a 2-phenyleth-lyl group, among others). Similarly, an "aralkylene group" is an aryl-substituted alkylene group having two free valencies at a single non-aromatic carbon atom of an arylalkane or a free valence at two non-aromatic carbon atoms of an arylalkane while an "aralkane group" is an aryl-substituted alkane group having one or more free valencies at a non-aromatic carbon atom(s) of an arylalkane. It should be noted that according the definitions provided herein, general aralkane groups include those having zero, one, or more than one hydrocarbyl substituent groups located on an aralkane aromatic hydrocarbon ring or ring system carbon atom and are members of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reaction zone" refers to any portion of equipment in which a desired reaction occurs, including but not limited to, a reactor, associated piping, associated pumps, and any other associated equipment. It should be noted that in some cases a "reactor" can also be a "reaction zone." The terms "reactor" and "reaction zone" can be qualified to refer to more specific "reactors" and "reaction zone" by use of additional qualifying terms. For example, the use of the term use of the term "oligomerization reactor" and "oligomerization reaction zone" indicates that the desired reaction within the reactor and/or reaction zone is an oligomerization reaction.

Within this specification, term "reaction zone" refers to the portion of a process, the associated equipment and associated process lines where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction system). For example, in terms of an oligomerization process, the reaction zone begins at the point where sufficient feedstock and active catalyst system is present under the sufficient reaction conditions to maintain oligomer product production at the desired rate and the reaction zone ends at a point where either the catalyst system is deactivated, sufficient feedstock is not present to sustain oligomer product production, or other reaction conditions are not sufficient to maintain the oligomer product production or the desired oligomer product production rate. Within this specification the "reaction zone" can comprise one or more reactor zone, one or more reactors, and associated equipment where all the necessary reaction components and reaction conditions are present such that the reaction can occur at a desired rate. The use of the term "oligomerization reaction zone" indicates that the desired reaction within the reaction zone is an oligomerization reaction.

The terms "room temperature" or "ambient temperature" are used herein to describe any temperature from 15° C. to 35° C. wherein no external heat or cooling source is directly applied. Accordingly, the terms "room temperature" and "ambient temperature" encompass the individual temperatures and any and all ranges, subranges, and combinations of subranges of temperatures from 15° C. to 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa). References to gaseous, liquid, and/or solid materials refer to the physical state of the material at 25° C. and atmospheric pressure unless otherwise specified.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using "comprising" or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Processes for forming oligomer products are described herein. Such processes generally comprise contacting ethylene and a catalyst system (or alternatively, contacting ethylene and the components of the catalyst system) to form an oligomer product under oligomerization conditions.

The term "reaction zone effluent" and its derivatives (e.g., oligomerization reaction zone effluent, trimerization reaction zone effluent, tetramerization reaction zone effluent, or trimerization and tetramerization reaction zone effluent) generally refers to all materials which exit the reaction zone. The materials that can exit the reaction zone include reaction feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all materials which exits the reaction zone, a reaction zone oligomer product effluent refers to only the oligomer product within the reaction zone effluent.

The term "oligomerization," and its derivatives, refers to processes which produce a mixture of products containing at least 70 weight percent products containing from 2 to 30 ethylene units. Similarly, as used herein an "oligomer" is a product that contains from 2 to 30 ethylene units while an "oligomerization product" or "oligomer product" includes all products made by the process including the "oligomers" and products which are not "oligomers" (e.g., products which contain more than 30 ethylene units). Further the terms "oligomer product" and "oligomerization product" can be used interchangeably.

The term "trimerization," and its derivatives, refers to a process which produces a mixture of products containing at least 70 weight percent products containing three and only three ethylene units. A "trimer" is a product which contains three and only three ethylene units while a "trimerization product" includes all products made by the trimerization process including trimers and products which are not trimers (e.g., dimers or tetramers). Generally, a "trimerization" process using ethylene produces an oligomer product containing at least 70 weight percent hexene(s).

The term "tetramerization," and its derivatives, refers to a process which produces a mixture of products containing at least 70 weight percent products containing four and only four ethylene units. A "tetramer" is a product which contains four and only four ethylene units while a "tetramerization product" includes all products made by the tetramerization process including tetramers and products which are not tetramers (e.g., dimers or trimers). Generally, a "tetramerization" process using ethylene produces an oligomer product containing at least 70 weight percent octene(s).

The term "trimerization and tetramerization," and its derivatives, refers to a process which produces a mixture of products containing at least 70 weight percent products containing three and/or four and only three and/or four ethylene units. A "trimerization and tetramerization product" includes all products made by the "trimerization and tetramerization" process including trimers, tetramers, and products which are not trimers or tetramers (e.g., dimers). Generally, a "trimerization and tetramerization" process using ethylene produces an oligomer product containing at least 70 weight percent hexene(s) and/or octene(s).

Unless otherwise specified, the terms "contacted," "combined," and "in the presence of" refer to any addition sequence, order, or concentration for contacting or combining two or more components of the process. Combining or contacting of components, according to the various methods described herein, can occur in one or more contact zones under suitable contact conditions such as temperature, pressure, contact time, flow rates, etc. The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact. The processes can be carried out in a batch or continuous process as can be suitable for a given aspect.

Use of the term "optionally" with respect to any element of a claim is intended to mean that the subject element is required, or alternatively, is not required. Both alternatives are intended to be within the scope of the claim.

Processes described herein can utilize steps, features, compounds and/or equipment which are independently described herein. The processes described herein may or may not utilize step identifiers (e.g., 1), 2), etc., a), b), etc., i), ii), etc., or first, second, etc., among others), feature identifiers (e.g., 1), 2), etc., a), b), etc., i), ii), etc., or first, second, etc., among others), and/or compound and/or composition identifiers (e.g., 1), 2), etc., a), b), etc., i), ii), etc., or first, second, etc., among others). However, it should be noted that processes described herein can have multiple steps, features (e.g., reagent ratios, formation conditions, among other considerations), and/or multiple compounds and/or compositions using no descriptor or sometimes having the same general identifier. Consequently, it should be noted that the processes described herein can be modified to use an appropriate step or feature identifier (e.g., 1), 2), etc., a), b), etc., i), ii), etc., or first, second, etc., among others), feature identifier (e.g., 1), 2), etc., a), b), etc., i), ii), etc., or first, second, etc., among others), and/or compound identifier (e.g., first, second, etc.) regardless of step, feature, and/or compound identifier utilized in a particular aspect described herein and that step or feature identifiers can be added and/or modified to indicate individual different steps/features/compounds utilized within the processes without detracting from the general disclosure.

The present disclosure relates to catalyst systems comprising an $N^2$-phosphinyl bicyclic amidine chromium salt complex; or alternatively, an $N^2$-phosphinyl bicyclic amidine and a chromium salt. In an aspect, the catalyst system can comprise, or consist essentially of, an $N^2$-phosphinyl bicyclic amidine chromium salt complex and an organoaluminum compound; or alternatively, an $N^2$-phosphinyl bicyclic amidine, a chromium salt, and an organoaluminum compound. The present disclosure also relates to processes comprising a) contacting i) ethylene and ii) a catalyst system comprising (a) (i) an $N^2$-phosphinyl bicyclic amidine chromium salt complex or (ii) a chromium salt and an $N^2$-phosphinyl bicyclic amidine and (b) an organoaluminum compound, and iii) optionally an organic reaction medium, and b) forming an oligomer product in a reaction zone. The $N^2$-phosphinyl bicyclic amidine chromium salt complex, the chromium salt, the $N^2$-phosphinyl bicyclic amidine, the organoaluminum compound, and the optional organic reaction medium which can be utilized in the catalyst system and processes are independently described herein and can be utilized in any combination and without limitation to describe the catalyst systems and processes of this disclosure.

Generally, the $N^2$-phosphinyl bicyclic amidines and $N^2$-phosphinyl bicyclic amidine chromium salt complexes encompassed by this disclosure have at least one $N^2$-phosphinyl bicyclic amidine group. In an aspect, the $N^2$-phosphinyl bicyclic amidines and $N^2$-phosphinyl bicyclic amidine chromium salt complexes can comprise only one $N^2$-phosphinyl bicyclic amidine group; or alternatively, can comprise only two $N^2$-phosphinyl bicyclic amidine groups. In an aspect, the $N^2$-phosphinyl bicyclic amidines, regardless of the number of $N^2$-phosphinyl bicyclic amidine groups, or structure, can be non-metallic (i.e., a non-metallic $N^2$-phosphinyl bicyclic amidine or a non-metallic compound having an $N^2$-phosphinyl bicyclic amidine group).

In an aspect, the $N^2$-phosphinyl bicyclic amidine can have Structure NPBA I or NPBA II. In an aspect, the $N^2$-phosphinyl bicyclic amidine chromium salt complex can have Structure NPBACr I or NPBACr II.

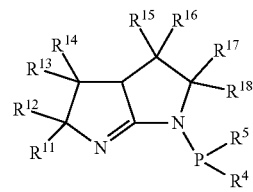

NPBA I

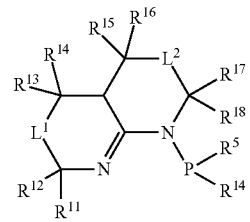

NPBA II

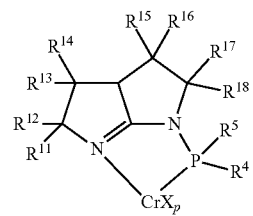

NPBACr I

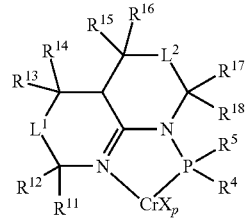

NPBACr II

Within the $N^2$-phosphinyl bicyclic amidine having Structure NPBA I and/or NPBA II, $R^{11}$, $R^{12}$, $R^{13}$, $R_{14}$, $R^{15}$, $R^{16}$, $R^{17}$, $R^{18}$, $L^1$, $L^2$, $R^4$, and $R^5$ are independent elements of the $N^2$-phosphinyl bicyclic amidine having Structure NPBA I and/or NPBA II and are independently described herein. The independent descriptions of $R^{11}$, $R^{12}$, $R^{13}$, $R^{14}$, $R^{15}$, $R^{16}$, $R^{17}$, $R^{18}$, $L^1$, $L^2$, $R^4$, and $R^5$ can be utilized without limitation, and in any combination, to describe the $N^2$-phosphinyl bicyclic amidine having Structure NPBA I and/or NPBA II which can be utilized in any aspect described herein. Within the $N^2$-phosphinyl bicyclic amidine chromium salt complex having Structure NPBACr I and/or NPBACr II, $R^{11}$, $R^{12}$, $R^{13}$, $R^{14}$, $R^{15}$, $R^{16}$, $R^{17}$, $R^{18}$, $L^1$, $L^2$, $R^4$, and $R^5$ of the $N^2$-phosphinyl bicyclic amidine and the chromium salt, $CrX_p$, are independent elements of the $N^2$-phosphinyl bicyclic amidine chromium salt complexes having Structure NPBACr I and/or NPBACr and are independently described herein. The independent description of $R^{11}$, $R^{12}$, $R^{13}$, $R^{14}$, $R^{15}$, $R^{16}$, $R^{17}$, $R^{18}$, $L^1$, $L^2$, $R^4$, $R^5$ and $CrX_p$ can be utilized without limitation, and in any combination, to describe the $N^2$-phosphinyl bicyclic amidine chromium salt complex having Structure NPBACr I and/or NPBACr II which can be utilized in any aspect described herein.

Generally, $R^{11}$, $R^{12}$, $R^{13}$, $R^{14}$, $R^{15}$, $R^{16}$, $R^{17}$, and $R^{18}$ of the $N^2$-phosphinyl bicyclic amidine structures and/or the $N^2$-phosphinyl bicyclic amidine chromium salt complex structures each independently can be hydrogen or an organyl group; alternatively, hydrogen or an organyl group consisting of inert functional groups; alternatively, a hydrogen or hydrocarbyl group; alternatively, an organyl group; alternatively, an organyl group consisting of inert functional groups; alternatively, a hydrocarbyl group; or alternatively, hydrogen. In an aspect, the organyl groups which can be utilized as a non-hydrogen $R^{11}$, $R^{12}$, $R^{13}$, $R^{14}$, $R^{15}$, $R^{16}$, $R^{17}$, and/or $R^{18}$ can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as a non-hydrogen $R^{11}$, $R^{12}$, $R^{13}$, $R^{14}$, $R^{15}$, $R^{16}$, $R^{17}$, and/or $R^{18}$ can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as a non-hydrogen $R^{11}$, $R^{12}$, $R^{13}$, $R^{14}$, $R^{15}$, $R^{16}$, $R^{17}$, and/or $R^{18}$ can be a $C_1$ to $C_{20}$, a $C_1$ to $C_{15}$, a $C_1$ to $C_{10}$, or a $C_1$ to $C_5$ hydrocarbyl group.

In an aspect, each non-hydrogen $R^{11}$, $R^{12}$, $R^{13}$, $R^{14}$, $R^{15}$, $R^{16}$, $R^{17}$, and/or $R^{18}$ of the $N^2$-phosphinyl bicyclic amidines and/or the $N^2$-phosphinyl bicyclic amidine chromium salt complexes independently can be an alkyl group, a substituted alkyl group, a cycloalkyl group, a substituted cycloalkyl group, an aryl group, a substituted aryl group, an aralkyl group, or a substituted aralkyl group; alternatively an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, any $R^{11}$, $R^{12}$, $R^{13}$, $R^{14}$, $R^{15}$, $R^{16}$, $R^{17}$, and/or $R^{18}$ alkyl group independently can be a $C_1$ to $C_{20}$, a $C_1$ to $C_{10}$, or a $C_1$ to $C_5$ alkyl group. In any aspect disclosed herein, any $R^{11}$, $R^{12}$, $R^{13}$, $R^{14}$, $R^{15}$, $R^{16}$, $R^{17}$, and/or $R^{18}$ substituted alkyl group independently can be a $C_1$ to $C_{20}$, a $C_1$ to $C_{10}$, or a $C_1$ to $C_5$ substituted alkyl group. In any aspect disclosed herein, any $R^{11}$, $R^{12}$, $R^{13}$, $R^{14}$, $R^{15}$, $R^{16}$, $R^{17}$, and/or $R^{18}$ cycloalkyl group independently can be a $C_4$ to $C_{20}$, a $C_4$ to $C_{15}$, or a $C_4$ to $C_{10}$ cycloalkyl group. In any aspect disclosed herein, any $R^{11}$, $R^{12}$, $R^{13}$, $R^{14}$, $R^{15}$, $R^{16}$, $R^{17}$, and/or $R^{18}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, any $R^{11}$, $R^{12}$, $R^{13}$, $R^{14}$, $R^{15}$, $R^{16}$, $R^{17}$, and/or $R^{18}$ aryl group independently can be a $C_6$ to $C_{20}$, a $C_6$ to $C_{15}$, or a $C_6$ to $C_{10}$ aryl group. In any aspect disclosed herein, any $R^{11}$, $R^{12}$, $R^{13}$, $R^{14}$, $R^{15}$, $R^{16}$, $R^{17}$, and/or $R^{18}$ substituted aryl group independently can be a $C_6$ to $C_{20}$, a $C_6$ to $C_{15}$, or a $C_6$ to $C_{10}$ substituted aryl group. In any aspect disclosed herein, any $R^{11}$, $R^{12}$, $R^{13}$, $R^{14}$, $R^{15}$, $R^{16}$, $R^{17}$, and/or $R^{18}$ aralkyl group independently can be a $C_7$ to $C_{20}$, a $C_7$ to $C_{15}$, or a $C_7$ to $C_{10}$ aralkyl group. In any aspect disclosed herein, any $R^{11}$, $R^{12}$, $R^{13}$, $R^{14}$, $R^{15}$, $R^{16}$, $R^{17}$, and/or $R^{18}$ substituted aralkyl group independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted non-hydrogen $R^{11}$, $R^{12}$, $R^{13}$, $R^{14}$, $R^{15}$, $R^{16}$, $R^{17}$ and/or $R^{18}$.

In an aspect, when any of $R^{11}$, $R^{12}$, $R^{13}$, $R^{14}$, $R^{15}$, $R^{16}$, $R^{17}$ and/or $R^{18}$ of the $N^2$-phosphinyl bicyclic amidine structures and the $N^2$-phosphinyl bicyclic amidine chromium salt complex structures are not hydrogen, each non-hydrogen $R^{11}$, $R^{12}$, $R^{13}$, $R^{14}$, $R^{15}$, $R^{16}$, $R^{17}$, and/or $R^{18}$ of the $N^2$-phosphinyl bicyclic amidines and/or the $N^2$-phosphinyl bicyclic amidine chromium salt complexes independently can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^{11}$, $R^{12}$, $R^{13}$, $R^{14}$, $R^{15}$, $R^{16}$, $R^{17}$, and/or $R^{18}$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as a non-hydrogen $R^{11}$, $R^{12}$, $R^{13}$, $R^{14}$, $R^{15}$, $R^{16}$, $R^{17}$ and/or $R^{18}$.

In an aspect, $L^1$ and $L^2$, of the $N^2$-phosphinyl bicyclic amidines and the $N^2$-phosphinyl bicyclic amidine chromium salt complexes having an $L^1$ and/or $L^2$, independently can an organylene group; alternatively, an organylene group consisting of inert functional groups; or alternatively, a hydrocarbylene group. The $L^1$ and/or $L^2$ organylene groups independently can be a $C_1$ to $C_{20}$, a $C_1$ to $C_{15}$, a $C_1$ to $C_{10}$, or a $C_1$ to $C_5$ organylene group. The $L^1$ and/or $L^2$ organylene groups consisting of inert functional groups independently can be a $C_1$ to $C_{20}$, a $C_1$ to $C_{15}$, a $C_1$ to $C_{10}$, or a $C_1$ to $C_5$ organylene group consisting of inert functional groups. The $L^1$ and/or $L^2$ hydrocarbylene groups independently can be a $C_1$ to $C_{20}$, a $C_1$ to $C_{15}$, a $C_1$ to $C_{10}$, or a $C_1$ to $C_5$ hydrocarbylene group.

In an aspect, $L^1$ and/or $L^2$ of the $N^2$-phosphinyl bicyclic amidines and the $N^2$-phosphinyl bicyclic amidine chromium salt complexes having an $L^1$ and/or $L^2$, independently can have any structure provided in Table 1. In some aspects, $L^1$ and/or $L^2$ can have Structure 1L, Structure 2L, Structure 3L, Structure 4L or Structure 5L. In some aspects, $L^1$ and/or $L^2$ can have Structure 2L, Structure 3L, or Structure 4L; alternatively, Structure 5L or Structure 6L. In other aspects, $L^1$ and/or $L^2$ can have Structure 1L; alternatively, Structure 2L; alternatively, Structure 3L; alternatively, Structure 4L; alternatively, Structure 5L; or alternatively Structure 6L.

TABLE 1

Structures for Linking Groups $L^1$ and/or $L^2$.

| —$(CR^{L1}R^{L2})_m$— | —$CR^{L1}R^{L2}_m$— | —$CR^{L3}R^{L4}$—$CR^{L5}R^{L6}$— |
|---|---|---|
| Structure 1L | Structure 2L | Structure 3L |
| —$CR^{L3}R^{L4}$—$CR^{L7}R^{L8}$—$CR^{L5}R^{L6}$— | —$CRL^{11}$=$CR^{L12}$— | —$CR^{L21}R^{L22}$—$CR^{23}$=$CR^{24}$— |
| Structure 4L | Structure 5L | Structure 6L |

Within the structures of Table 1, the undesignated valences of $L^1$ and/or $L^2$ represent the points at which $L^1$ and/or $L^2$, when present in the $N^2$-phosphinyl bicyclic amidines and/or the $N^2$-phosphinyl bicyclic amidine chromium salt complexes, attach to the designated atoms of the $N^2$-phosphinyl bicyclic amidine and/or the $N^2$-phosphinyl bicyclic amidine chromium salt complex. In an aspect, m for the $L^1$ and/or $L^2$ linking group having Structure 1L independently can be an integer ranging from 1 to 5; alternatively, 1 to 3; alternatively, 1; alternatively, 2; or alternatively, 3. In an aspect, $R^{L1}$ and $R^{L2}$ of the linking group having Structure 1L or Structure 2L, $R^{L3}$, $R^{L4}$, $R^{L5}$, and $R^{L6}$ of the linking group having Structure 3L, $R^{L3}$, $R^{L4}$, $R^{L5}$, $R^{L6}$, $R^{L7}$, and $R^{L8}$ of the linking group having Structure 4L, $R^{L11}$ and $R^{L12}$ of the linking group having Structure 5L, and $R^{L21}$, $R^{L22}$, $R^{L23}$, and $R^{L24}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an aspect, $L^1$ and/or $L^2$ independently can be a methylene group (—$CH_2$—), an eth-1,2-ylene group (—$CH_2CH_2$—), an ethen-1,2-ylene group (—CH=CH—), a prop-1,3-ylene group (—$CH_2CH_2CH_2$—), a prop-1,2-ylene group (—CH(CH$_3$)CH$_2$—), a propen-1,3-ylene group (—$CH_2$CH=CH—), a propen-1,2-ylene group (—CH=CH(CH$_3$)—), a but-1,4-ylene group (—$CH_2CH_2CH_2CH_2$—), a but-1,3-ylene group (—$CH_2CH_2$CH(CH$_3$)—), a 2-methylprop-1,3-ylene group (—$CH_2$CH(CH$_3$)CH$_2$—), a 2-methylprop-1,2-ylene group (—C(CH$_3$)$_2$CH$_2$—), a but-1,2-en-1,4-ylene group (—$CH_2CH_2$CH=CH—), a but-1,2-en-1,3-ylene group (—CH(CH$_3$)CH=CH—), a but-2,3-en-1,4-ylene group (—$CH_2$CH=CHCH$_2$—), or a 2-methylpropen-1,3-ylene group (—$CH_2$C(CH$_3$)=CH—). In some non-limiting aspects, L' and/or $L^2$ be a methylene group (—$CH_2$—), an eth-1,2-ylene group (—$CH_2CH_2$—), an ethen-1,2-ylene group (—CH=CH—), a prop-1,3-ylene group (—$CH_2CH_2CH_2$—, —), a prop-1,2-ylene group (—CH(CH$_3$)CH$_2$—), a propen-1,3-ylene group (—$CH_2$CH=CH—), a propen-1,2-ylene group (—CH=CH(CH$_3$)—), a but-1,3-ylene group (—$CH_2CH_2$CH(CH$_3$)—), a 2-methylprop-1,3-ylene group (—$CH_2$CH(CH$_3$)CH$_2$—), a 2-methylprop-1,2-ylene group (—C(CH$_3$)$_2$CH$_2$—), or a 2-methylpropen-1,3-ylene group (—$CH_2$C(CH$_3$)=CH—); alternatively, a methylene group (—$CH_2$—), an eth-1,2-ylene group (—$CH_2CH_2$—), a prop-1,3-ylene group (—$CH_2CH_2CH_2$—), a prop-1,2-ylene group (—CH(CH$_3$)CH$_2$—), a but-1,3-ylene group (—$CH_2CH_2$CH(CH$_3$)—), a 2-methylprop-1,3-ylene group (—$CH_2$CH(CH$_3$)CH$_2$—), or a 2-methylprop-1,2-ylene group (—C(CH$_3$)$_2$CH$_2$—); alternatively, a methylene group (—$CH_2$—), an eth-1,2-ylene group (—$CH_2CH_2$—), or a prop-1,3-ylene group (—$CH_2CH_2CH_2$—); alternatively, a methylene group (—$CH_2$—), or an eth-1,2-ylene group (—$CH_2CH_2$—); alternatively, a methylene group (—$CH_2$—); alternatively, an eth-1,2-ylene group (—$CH_2CH_2$—); or alternatively, a prop-1,3-ylene group (—$CH_2CH_2CH_2$—). The specific $L^1$s and/or $L^2$s are given their proper names. However, these proper names are not intended to imply which atoms of the $N^2$-phosphinyl bicyclic amidines and/or the $N^2$-phosphinyl bicyclic amidine chromium salt complexes the undesignated valencies are attached to. The undesignated valencies can be attached to either of the two $N^2$-phosphinyl bicyclic amidines or the $N^2$-phosphinyl bicyclic amidine chromium salt complexes designated atoms as long as it provides a proper $N^2$-phosphinyl bicyclic amidine or the $N^2$-phosphinyl bicyclic amidine chromium salt complex unless otherwise specified.

Generally, $R^4$ and/or $R^5$ of the $N^2$-phosphinyl bicyclic amidines and/or the $N^2$-phosphinyl bicyclic amidine chromium salt complexes independently can be an organyl group; alternatively, an organyl group consisting of inert functional groups; or alternatively, a hydrocarbyl group. In an aspect, the $R^4$ and/or $R^5$ organyl groups can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^4$ and/or $R^5$ hydrocarbyl groups can be a, a $C_1$ to $C_{20}$, a $C_1$ to $C_{15}$, a $C_1$ to $C_{10}$, or a $C_1$ to $C_5$ hydrocarbyl group. In an aspect, $R^4$ and/or $R^5$ of the $N^2$-phosphinyl bicyclic amidines and/or the $N^2$-phosphinyl bicyclic amidine chromium salt complexes independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, the $R^4$ and/or $R^5$ alkyl groups independently can be a $C_1$ to $C_{20}$, a $C_1$ to $C_{10}$, or a $C_1$ to $C_5$ alkyl group. In any aspect disclosed herein, the $R^4$ and/or $R^5$ substituted alkyl groups independently can be a $C_1$ to $C_{20}$, a $C_1$ to $C_{10}$, or $C_1$ to $C_5$ substituted alkyl group. In any aspect disclosed herein, the $R^4$ and/or $R^5$ cycloalkyl groups independently can be a $C_4$ to $C_{20}$, a $C_4$ to $C_{15}$, or a $C_4$ to $C_{10}$ cycloalkyl group. In any aspect disclosed herein, the $R^4$ and/or $R^5$ substituted cycloalkyl groups independently can be a $C_4$ to $C_{20}$, a $C_4$ to $C_{15}$, or a $C_4$ to $C_{10}$ substituted cycloalkyl group. In any aspect disclosed herein, the $R^4$ and/or $R^5$ aryl groups independently can be a $C_6$ to $C_{20}$, a $C_6$ to $C_{15}$, or a $C_6$ to CH) aryl group. In any aspect disclosed herein, the $R^4$ and/or $R^5$ substituted aryl group independently can be a $C_6$ to $C_{20}$, a $C_6$ to $C_{15}$, or a $C_6$ to $C_{10}$ substituted aryl group. In any aspect disclosed herein, the $R^4$ and/or $R^5$ aralkyl groups independently can be a $C_7$ to $C_{20}$, a $C_7$ to $C_{15}$, or a $C_7$ to $C_{10}$ aralkyl group. In any aspect disclosed herein, the $R^4$ and/or $R^5$ substituted aryl groups independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a 2-methyl-1-propyl group, a tert-butyl (2-methyl-2-propyl) group, or a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. When the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect, $R^4$ and $R^5$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. When the substituted phenyl group (general or specific) has more the one substituent, the substituents can be the same or different; alternatively, all the substituents of a multi-substituted phenyl group can be the same; or alternatively, all the substituents of a multi-substituted phenyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^5$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

In further aspects, $R^4$ and $R^5$ can be joined to form a ring or a ring system containing the phosphorus atom. The joining of $R^4$ and $R^5$ can be designated as $L^{45}$ and can be an organylene group; alternatively, an organylene group consisting of inert functional groups; alternatively, a hydrocarbylene group; or alternatively, an alkylene group. In an aspect, the $L^{45}$ organylene group, when present, can be a $C_4$ to $C_{30}$, a $C_4$ to $C_{20}$, a $C_4$ to $C_{15}$, or a $C_4$ to $C_{10}$ organylene group. In an aspect, the $L^{45}$ organylene group consisting of inert functional groups, when present, can be a $C_4$ to $C_{30}$, a $C_4$ to $C_{20}$, a $C_4$ to $C_{15}$, or a $C_4$ to $C_{10}$ organylene group consisting of inert functional groups. In an aspect, the $L^{45}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{45}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{45}$ can be a but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyOdipheylene group, or a 2,2'-(1,2-ethandiyl) diphenylene group.

Various aspects described herein refer to non-hydrogen substituents such as halogen (or halo, halide), hydrocarbyl, hydrocarboxy, alkyl, and/or alkoxy substituents. In an aspect, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group, or an aralkoxy group. In an aspect, any alkoxy substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an aspect, any aralkoxy substituent independently can be benzoxy group.

Various aspects disclosed herein can utilize a chromium salt or an $N^2$-phosphinyl bicyclic amidine chromium salt complex. Generally, the chromium salt and/or the chromium salt of the $N^2$-phosphinyl bicyclic amidine chromium salt complex can have the formula $CrX_p$ where X represents a monoanionic ligand and p represents the number of monoanionic ligands (and the oxidation state of the chromium in the chromium compound). The monoanionic ligand (X) and p are independent elements of the chromium salt and the chromium salt portion of the $N^2$-phosphinyl bicyclic amidine chromium salt complex and are independently described herein. These independent descriptions of the monoanionic ligand (X) and p can be utilized without limitation, and in any combination, to further describe the chromium salt and/or the chromium salt of the $N^2$-phosphinyl bicyclic amidine chromium salt complex which can be utilized in various aspects described herein.

Generally, the chromium atom of the chromium salt ($CrX_p$) or the chromium salt of the $N^2$-phosphinyl bicyclic amidine chromium salt complex can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound ($CrX_p$) can have an oxidation state of +1; alternatively, +2; alternatively, +3; or alternatively, +4.

The monoanion, X, of the chromium salt and/or the chromium salt of the $N^2$-phosphinyl bicyclic amidine chromium salt complex can be any monoanion. In an aspect, the monoanion (X) can be a halide, a carboxylate, a β-diketonate, a hydrocarboxide, a nitrate, or a chlorate. In some aspects, the monoanion (X) can be a halide, a carboxylate, a β-diketonate, or a hydrocarboxide. In any aspect, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion (X) can be a halide, a carboxylate, a β-diketonate, or an alkoxide; or alternatively, a halide or a β-diketonate. In other aspects, the monoanion (X) can be a halide; alternatively, a carboxylate; alternatively, a β-diketonate; alternatively, a hydrocarboxide; alternatively, an alkoxide; or alternatively, an aryloxide. In an aspect, the number of monoanions can be from 2 to 6; alternatively, from 2 to 4; alternatively, from 2 to 3; alternatively, 1; alternatively, 2; alternatively, 3; or alternatively, 4.

Generally, each halide of the chromium salt ($CrX_p$) or the chromium salt of the $N^2$-phosphinyl bicyclic amidine chromium salt complex independently can be fluorine, chlorine, bromine, or iodine; or alternatively, chlorine, bromine, or iodine. In an aspect, each halide monoanion of the chromium compound can be chlorine; alternatively, bromine; or alternatively, iodine.

Generally, each carboxylate of the chromium salt ($CrX_p$) or the chromium salt of the $N^2$-phosphinyl bicyclic amidine chromium salt complex independently can be a $C_1$ to $C_{20}$ or $C_1$ to $C_{10}$ carboxylate. In an aspect, each carboxylate independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, each carboxylate can be triflate (trifluoroacetate).

Generally, each β-diketonate of the chromium salt ($CrX_p$) or the chromium salt of the $N^2$-phosphinyl bicyclic amidine chromium salt complex independently can be a $C_1$ to $C_{20}$ or $C_1$ to $C_{10}$ diketonate. In an aspect, each β-diketonate independently can be acetylacetonate (i.e., 2,4-pentanedionate), hexafluoroacetylacetonate (i.e., 1, 1,1,5,5,5-hexafluoro-2,4-pentanedionate), or benzoylacetonate); alternatively, acetylacetonate; alternatively, hexafluoroacetylacetonate; or alternatively, benzoylacetonate.

Generally, each hydrocarboxide of the chromium salt ($CrX_p$) or the chromium salt of the $N^2$-phosphinyl bicyclic amidine chromium salt complex independently can be a $C_1$ to $C_{20}$ or $C_1$ to $C_{10}$ hydrocarboxide. In an aspect, each hydrocarboxide independently can be a $C_1$ to $C_{20}$ or $C_1$ to $C_{10}$ alkoxide; or alternatively, a $C_6$ to $C_{20}$ or $C_6$ to $C_{10}$ aryloxide. In an aspect, each alkoxide independently can be methoxide, ethoxide, a propoxide, or a butoxide; alternatively, methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In some non-limiting aspects, the chromium salt ($CrX_p$) or the chromium salt of the $N^2$-phosphinyl bicyclic amidine chromium salt complex can comprise, can consist essentially of, or consist of, a chromium(II) halide, a chromium (II) carboxylate, or a chromium(II) β-diketonate; or alternatively, a chromium(III) halide, a chromium(III) carboxylate, or a chromium(III) β-diketonate. In other non-limiting aspects, the chromium salt ($CrX_p$) or the chromium salt of the $N^2$-phosphinyl bicyclic amidine chromium salt complex can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate. Halides, carboxylates, β-diketonates are independently described herein and these halides, carboxylates, β-diketonate and these independently described halides, carboxylates, β-diketonates can be utilized without limitation and in any combination to further described the chromium salt ($CrX_p$) or the chromium salt of the $N^2$-phosphinyl bicyclic amidine chromium salt complex. In further non-limiting aspects, the chromium salt ($CrX_p$) or the chromium salt of the $N^2$-phosphinyl bicyclic amidine chromium salt complex can comprise, can consist essentially of, or consist of, chromium(II) chloride, chromium(III) chloride, chromium(II) fluoride, chromium(III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium (II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate; alternatively, chromium (III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; alternatively, chromium(III) chloride, or chromium(III) acetylacetonate; alternatively, chromium(III) chloride; or alternatively, chromium(III) acetylacetonate.

In an aspect, the $N^2$-phosphinyl bicyclic amidine can have Structure NPBA 1, NPBA 2, NPBA 3, NPBA 4, or NPBA 5; alternatively, Structure NPBA 1, NPBA 2, or NPBA 3; alternatively, Structure NPBA 1; alternatively, Structure NPBA 2; alternatively, Structure NPBA 3; alternatively, Structure NPBA 4; or alternatively NPBA 5.

NBPA 1

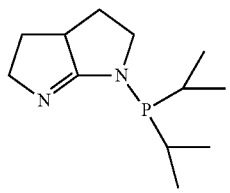

NBPA 2

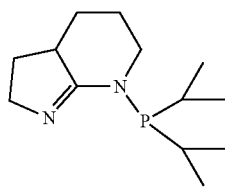

NBPA 3

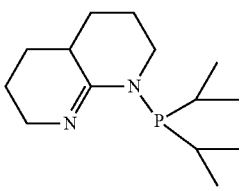

NBPA 4

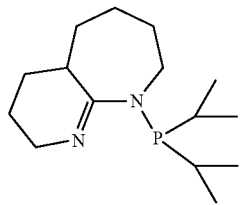

NBPA 5

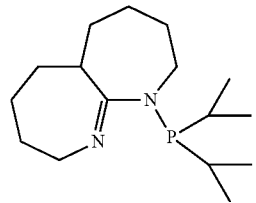

In an aspect, the $N^2$-phosphinyl bicyclic amidine chromium salt complex can have Structure NPBACr 1, NPBACr 2, NPBACr 3, NPBACr 4, or NPBACr 5; alternatively, Structure NPBACr 1, NPBACr 2, or NPBACr 3; alternatively, Structure NPBACr 1; alternatively, Structure NPBACr 2; alternatively, Structure NPBACr 3; alternatively, Structure NPBACr 4; or alternatively NPBACr 5.

NPBACr 1

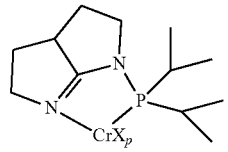

NPBACr 1

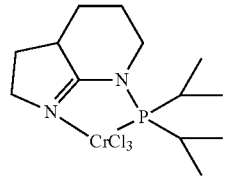

NPBACr 3

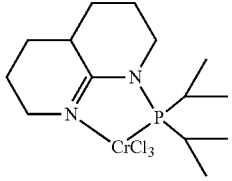

NPBACr 4

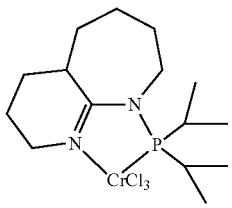

NPBACr 5

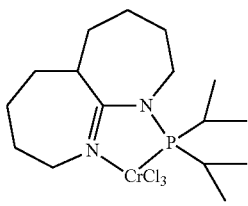

While not identified for the chromium salts and shown in the $N^2$-phosphinyl bicyclic amidine chromium salt complex structures provided herein, one of ordinary skill in the art will recognize that a neutral ligand, Q, can be associated with the chromium salts the $N^2$-phosphinyl bicyclic amidine chromium salt complexes described/depicted herein. Additionally, it should be understood that while the chromium salts and the $N^2$-phosphinyl bicyclic amidine chromium salt complexes described/depicted/provided herein do not formally show the presence of a neutral ligand, the chromium salts and/or the $N^2$-phosphinyl bicyclic amidine chromium salt complexes having neural ligands (e.g., nitriles and ethers, among others) are implicitly and fully contemplated as potential the chromium salts and/or the $N^2$-phosphinyl bicyclic amidine chromium salt complexes that can be utilized in the catalyst system used in aspects of the herein described inventions.

Generally, the neutral ligand of any chromium salt and/or $N^2$-phosphinyl bicyclic amidine chromium salt complex, when present, independently can be any neutral ligand that forms an isolatable compound with the chromium salt and/or $N^2$-phosphinyl bicyclic amidine chromium salt complex. In an aspect, each neutral ligand independently can be a nitrile or an ether; alternatively, a nitrile; or alternatively, an ether. The number of neutral ligands, q, can be any number that forms an isolatable compound with the chromium salt and/or $N^2$-phosphinyl bicyclic amidine chromium salt complex. In an aspect, the number of neutral ligands can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$, or $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile Generally, each ether ligand independently can be a $C_2$ to $C_{40}$, $C_2$ to $C_{30}$, or $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof, alternatively, dimethyl ether, diethyl ether, a dipropyl ether, a dibutyl ether, methyl ethyl ether, a methyl propyl ether, a methyl butyl ether, or any combination thereof, tetrahydrofuran, a dihydrofuran, 1,3-dioxolane, tetrahydropyran, a dihydropyran, a pyran, a dioxane, or any combination thereof, furan, benzofuran, isobenzofuran, dibenzofuran, or any combination thereof, diphenyl ether, a ditolyl ether, or any combination thereof, alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Throughout this disclosure, the monomeric form of the $N^2$-phosphinyl bicyclic amidine chromium salt complex has been depicted. It should be noted that while not explicitly shown, the $N^2$-phosphinyl bicyclic amidine chromium salt complex can exist as dimeric structures having two mono-anion ligands bridging two chromium atoms. Consequently, while the monomeric $N^2$-phosphinyl bicyclic amidine chromium salt complex is depicted herein, these structures do not necessarily imply that a dimeric form of the $N^2$-phosphinyl bicyclic amidine chromium salt complex having bridging monomeric ligands are not formed and/or utilized.

In an aspect, the organoaluminum compound which can be utilized in the catalyst systems and processes described herein can comprise an aluminoxane, an alkylaluminum compound, or any combination thereof; alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In a non-limiting aspect, the aluminoxane can have a repeating unit characterized by Formula I:

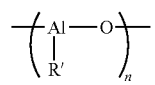

Formula I wherein R' is a linear or branched alkyl group. Alkyl groups for organoaluminum compounds are independently described herein and can be utilized without limitation to further describe the aluminoxanes having Formula I. Generally, n of Formula I can be greater than 1; or alternatively, greater than 2. In an aspect, n can range from 2 to 15; or alternatively, from 3 to 10.

In an aspect, each halide of any alkylaluminum halide disclosed herein can independently be fluoride, chloride, bromide, or iodide; or alternatively, chloride, bromide, or iodide. In an aspect, each halide of any alkylaluminum halide disclosed herein can be fluoride; alternatively, chloride; alternatively, bromide; or alternatively, iodide.

In an aspect, each alkyl group of any organoaluminum compound disclosed herein (alkylaluminum trialkylaluminum, alkylaluminum halide, alkylaluminum alkoxide or aluminoxane, among others) independently can be a $C_1$ to $C_{20}$, $C_1$ to $C_{10}$, or $C_1$ to $C_6$ alkyl group. In an aspect, each alkyl group of any organoaluminum compound disclosed herein independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some aspects, each alkyl group of any organoaluminum compound disclosed herein independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$, $C_1$ to $C_{10}$, or $C_1$ to $C_6$ alkoxy group. In an aspect, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some aspects, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, useful trialkylaluminum compounds can include trimethylaluminum, triethylaluminum, tripropylaluminum, tributylaluminum, trihexylaluminum, trioctylaluminum, or mixtures thereof. In some non-limiting aspects, useful trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting aspects, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting aspect, useful alkylaluminum halides can include diethylaluminum chloride, diethylaluminum bromide, ethylaluminum dichloride, ethylaluminum sesquichloride, and mixtures thereof. In some non-limiting aspects, useful alkylaluminum halides can include diethylaluminum chloride, ethylaluminum dichloride, ethylaluminum sesquichloride, and mixtures thereof. In other non-limiting aspects, useful alkylaluminum halides can include diethylaluminum chloride; alternatively, diethylaluminum bromide; alternatively, ethylaluminum dichloride; or alternatively, ethylaluminum sesquichloride.

In a non-limiting aspect, useful aluminoxanes can include methylaluminoxane (MAO), ethylaluminoxane, a modified methylaluminoxane (e.g., a MMAO), n-propylaluminoxane, isopropyl-aluminoxane, n-butylaluminoxane, sec-butylaluminoxane, iso-butylaluminoxane, t-butylaluminoxane, 1-pentylaluminoxane, 2-pentylaluminoxane, 3-pentylaluminoxane, isopentylaluminoxane, neopentylaluminoxane, or mixtures thereof; In some non-limiting aspects, useful aluminoxanes can include methylaluminoxane (MAO), a modified methylaluminoxane (e.g., a MMAO), isobutyl aluminoxane, t-butylaluminoxane, or mixtures thereof. In other non-limiting aspects, useful aluminoxanes can include methylaluminoxane (MAO); alternatively, ethylaluminoxane; alternatively, a modified methylaluminoxane (e.g., a MMAO); alternatively, n-propylaluminoxane; alternatively, isopropylaluminoxane; alternatively, n-butylaluminoxane; alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentylaluminoxane; alternatively, isopentylaluminoxane; or alternatively, neopentylaluminoxane.

In an aspect, the catalyst system can have any organoaluminum compound and the $N^2$-phosphinyl bicyclic amidine chromium salt complex (or alternatively, the chromium salt of the $N^2$-phosphinyl bicyclic amidine ratio that can form an active catalyst system. In an aspect, the catalyst system can have a minimum aluminum of the organoaluminum compound to chromium of the $N^2$-phosphinyl bicyclic amidine chromium salt complex (or alternatively, chromium of the chromium salt in conjunction with the $N^2$-phosphinyl bicyclic amidine molar ratio (i.e., minimum Al to Cr molar ratio) of 10:1, 50:1, 75:1, or 100:1; alternatively or additionally, a maximum aluminum of the organoaluminum compound to chromium of the in conjunction with the $N^2$-phosphinyl bicyclic amidine chromium salt complex (or alternatively, chromium of the chromium salt in conjunction with the $N^2$-phosphinyl bicyclic amidine molar ratio (i.e., maximum Al to Cr molar ratio) of 5,000:1, 3,000:1, 2,000:1, 1,500:1, or 1,000:1. In an aspect, the catalyst system can have an Al to Cr molar ratio ranging from any minimum Al to Cr molar ratio disclosed herein to any maximum Al to Cr molar ratio disclosed herein. In a non-limiting aspect, the Al to Cr molar ratio can range from 10:1 to 5,000:1, from 50:1 to 3,000:1, from 75:1 to 2,000:1, from 100:1 to 2,000:1, or from 100:1 to 1,000:1. Other Al to Cr molar ratio ranges that can be utilized are readily apparent to those skilled in the art with the aid of this disclosure.

When the catalyst system utilizes an $N^2$-phosphinyl bicyclic amidine, a chromium salt, and an organoaluminum compound, the catalyst system can have (or the catalyst system can be formed at), the oligomer product can be formed at, the reaction zone can have, or the reaction zone can operate at any $N^2$-phosphinyl bicyclic amidine to chromium of the chromium salt equivalent ratio which can form an oligomer product. In an aspect, the minimum $N^2$-phosphinyl bicyclic amidine to chromium of the chromium salt molar ratio can be 0.8:1, 0.9:1, or 0.95:1; alternatively or additionally, the maximum $N^2$-phosphinyl bicyclic amidine to chromium of the chromium salt molar ratio can be 4:1, 2:1, 1.5:1, or 1.1:1. In an aspect, the catalyst system can have (or the catalyst system can be formed at), the oligomer product can be formed at, the reaction zone can have, or the reaction zone can operate at an $N^2$-phosphinyl bicyclic amidine to chromium of the chromium salt molar ratio in the range of any minimum $N^2$-phosphinyl bicyclic amidine to chromium of the chromium salt molar ratio disclosed herein to any maximum $N^2$-phosphinyl bicyclic amidine to chromium of the chromium salt molar ratio disclosed herein. In a non-limiting aspects, the $N^2$-phosphinyl bicyclic amidine to chromium of the chromium salt molar ratio can be in the range of 0.8:1 to 4:1, from 0.9:1 to 2:1, from 0.9:1 to 1.5:1, from 0.95:1 to 1.5:1, or from 0.95:1 to 1.1:1. Other $N^2$-phosphinyl bicyclic amidine to chromium of the chromium salt molar ratio ranges that can be utilized are readily apparent to those skilled in the art with the aid of this disclosure.

In an aspect, the processes described herein can comprise: a) contacting ethylene and a catalyst system; and b) forming an oligomer product. In some aspects, the processes described herein can comprise: a) contacting ethylene, hydrogen, and a catalyst system; and b) forming an oligomer product. In some aspects, the oligomer product can be formed under conditions capable of forming an oligomer product. In some aspects, the oligomer product can be formed in a reaction zone. In an aspect, the process can be an ethylene oligomerization process; alternatively, an ethylene trimerization process; alternatively, an ethylene tetramerization process; or alternatively, an ethylene trimerization and tetramerization process. In an aspect, the catalyst system can be formed in an organic liquid medium. In an aspect, the oligomer product can be formed in (or the reaction zone can include) an organic reaction medium. Generally, the organic liquid medium in which the catalyst system can be formed and the organic reaction medium in which the olefin and the catalyst system can be contacted (or alternatively, in which the oligomer product can be formed) can be the same; or alternatively, can be different. The catalyst system, the conditions under which the oligomer product can be formed (or alternatively, the conditions under which the reaction zone can operate), the organic liquid medium, the organic reaction medium, and features of the oligomer product are independently described herein and can be utilized in any combination, and without limitation, to further describe the processes described herein.

In an aspect, the processes described herein can comprise: a) forming a catalyst system mixture comprising an $N^2$-phosphinyl bicyclic amidine chromium salt complex and an organoaluminum compound (or alternatively, forming a catalyst system mixture comprising a chromium salt and $N^2$-phosphinyl bicyclic amidine, a chromium salt, and an organoaluminum compound); b) contacting the catalyst system mixture with ethylene; and c) forming an oligomer product. In some aspects, the step of contacting the catalyst system mixture with ethylene can be a step of contacting the catalyst system mixture with ethylene and hydrogen. In some aspects, the catalyst system mixture can further comprise an organic liquid medium. In some aspects, the catalyst system mixture and ethylene, and optionally hydrogen, can be contacted in or with an organic reaction medium. In an aspect, the process can comprise: a) forming a catalyst system mixture comprising, or consisting essentially of, the $N^2$-phosphinyl bicyclic amidine chromium salt complex, an organoaluminum compound, and an organic liquid medium (or alternatively, comprising the $N^2$-phosphinyl bicyclic amidine, a chromium salt, an organoaluminum compound, and an organic liquid medium); b) contacting the catalyst system mixture with ethylene and an organic reaction medium; and c) forming an oligomer product. In some aspects, the step of contacting the catalyst system mixture with ethylene and the organic liquid medium can be a step of contacting the catalyst system mixture with ethylene, an organic reaction medium, and hydrogen. In some aspects, the organic liquid medium and the organic reaction medium can be the same; or alternatively, the organic liquid medium and the organic reaction medium can be different. In some aspects, the oligomer product can be formed in a reaction zone. In some aspects, the oligomer product can be formed under conditions capable of forming an oligomer product. The $N^2$-phosphinyl bicyclic amidine, the chromium salt, the $N^2$-phosphinyl bicyclic amidine chromium salt complex, the organoaluminum compound, the organic liquid medium, the organic reaction medium, the conditions under which the oligomer product can be formed (or alternatively, the conditions under which the reaction zone can operate), and features of the oligomer product (among other independently described catalyst system and process features) are independently described herein and can be utilized, without limitation, and in any combination, to further describe the processes disclosed herein.

In an aspect, the processes described herein can comprise: a) forming a composition comprising an $N^2$-phosphinyl bicyclic amidine chromium salt complex (or alternatively, comprising an $N^2$-phosphinyl bicyclic amidine and a chromium salt); b) forming a mixture comprising ethylene and an organoaluminum compound; c) contacting the composition of step a) and the mixture of step b); and d) forming an oligomer product. In some aspects, the mixture comprising ethylene and the organoaluminum compound can further comprise hydrogen. In some aspects, the composition comprising the $N^2$-phosphinyl bicyclic amidine chromium salt complex (or alternatively, comprising the $N^2$-phosphinyl bicyclic amidine and the chromium salt) can further comprise an organic liquid medium. In some aspects, the mixture comprising ethylene, an organoaluminum compound, and optionally hydrogen, can further comprise an organic reaction medium. In an aspect, the process can comprise: a) forming a composition comprising, or consisting essentially of, the $N^2$-phosphinyl bicyclic amidine chromium salt complex and an organic liquid medium (or alternatively, comprising the $N^2$-phosphinyl bicyclic amidine, a chromium salt, and an organic liquid medium); b) forming a mixture comprising ethylene, an organoaluminum compound, optionally hydrogen, and an organic reaction medium; c) contacting the composition of step a) and the mixture of step b); and d) forming an oligomer product. In some aspects, the organic liquid medium and the organic reaction medium can be the same; or alternatively, the organic liquid medium and the organic reaction medium can be different. In some aspects, the oligomer product can be formed in a reaction zone. In some aspects, the oligomer product can be formed under conditions capable of forming an oligomer product. The $N^2$-phosphinyl bicyclic amidine, the chromium salt, the $N^2$-phosphinyl bicyclic amidine chromium salt complex, the organoaluminum compound, the organic liquid medium, the organic reaction medium, the conditions under which the oligomer product can formed (or alternatively, the conditions under which the reaction zone can operate), and features of the oligomer product (among other composition, mixture, oligomer product and process features) are independently described herein and can be utilized, without limitation, and in any combination, to further describe the processes described herein.

In an aspect, the processes described herein can comprise: a) contacting ethylene and a catalyst system comprising an $N^2$-phosphinyl bicyclic amidine chromium salt complex (or alternatively, contacting an $N^2$-phosphinyl bicyclic amidine and a chromium salt); and b) forming an oligomer product in a reaction zone. In some aspects, the processes described herein can comprise, a) contacting ethylene, hydrogen, and a catalyst system comprising the $N^2$-phosphinyl bicyclic amidine chromium salt complex (or alternatively, contacting the $N^2$-phosphinyl bicyclic amidine and a chromium salt); and b) forming an oligomer product in a reaction zone. In other aspects, the processes described herein can comprise: a) contacting ethylene and a catalyst system comprising the $N^2$-phosphinyl bicyclic amidine chromium salt complex and an organoaluminum compound (or alternatively, the $N^2$-phosphinyl bicyclic amidine and a chromium salt and an organoaluminum compound); and b) forming an oligomer product in a reaction zone. In yet other aspects, the processes described herein can comprise, a) contacting ethylene, hydrogen, and a catalyst system comprising the $N^2$-phosphinyl bicyclic amidine chromium salt complex and an organoaluminum compound (or alternatively, contacting an $N^2$-phosphinyl bicyclic amidine, a chromium salt, and an organoaluminum compound); and b) forming an oligomer product in a reaction zone. In an aspect, the respective processes can further comprise forming a catalyst system mixture comprising the catalyst system components. In some aspects, the catalyst system mixture can be (or can be formed in) an organic liquid medium. In other aspects of the respective processes, the oligomer product can be formed in (or the reaction zone can include) an organic reaction medium. In some aspects, the organic liquid medium and the organic reaction medium can be the same; or alternatively, the organic liquid medium and the organic reaction medium can be different. The $N^2$-phosphinyl bicyclic amidine, the chromium salt, the $N^2$-phosphinyl bicyclic amidine chromium salt complex, the organoaluminum compound, the organic liquid medium, the organic reaction medium, the conditions under which the oligomer product can be formed (or alternatively, the conditions under which the reaction zone can operate), and features of the oligomer product (among other composition, mixture, oligomer product, and process features) are independently described herein and can be utilized, without limitation, and in any combination, to further describe the processes described herein.

In an aspect, the processes described herein can be a batch process or a continuous process. In some aspects, the reaction zone of any process described herein can comprise any reactor which can oligomerize, trimerize, tetramerize, or trimerize and tetramerize ethylene to an oligomer product. In some aspects, the reaction zone can comprise one or more reactors. In some aspects, the reaction zone can comprise a stirred tank reactor, a plug flow reactor, or any combination thereof; alternatively, a stirred tank reactor; or alternatively, a plug flow reactor. In an aspect, the reaction zone of any process described herein can comprise an autoclave reactor, a continuous stirred tank reactor, a loop reactor, a gas phase reactor, a solution reactor, a tubular reactor, a recycle reactor, a bubble reactor, or any combination thereof; alternatively, an autoclave reactor; alternatively, a stirred tank reactor; alternatively, a loop reactor; alternatively, a gas phase reactor; alternatively, a solution reactor; alternatively, a tubular reactor; alternatively, a recycle reactor; or alternatively, a bubble reactor. In some aspects, the reaction zone can comprise multiple reactors; or alternatively, only one reactor. When multiple reactors are present, each of the reactors can be the same; or alternatively, two or more of the reactors can be different. The reaction zone can comprise single or multiple reactors of any type disclosed herein operating in batch or continuous mode and/or in series or parallel.

The processes described herein can use an organic liquid medium and/or an organic reaction medium. Generally, the organic liquid medium and/or the organic reaction medium can act as a solvent and/or a diluent in the processes described herein. In an aspect, the organic liquid medium and/or the organic reaction medium can be a hydrocarbon, a halogenated hydrocarbon, or a combination thereof. Hydrocarbons and halogenated hydrocarbons which can be used as the organic liquid medium and/or the organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be used as the organic liquid medium and/or the organic reaction medium include $C_3$ to $C_{20}$, $C_4$ to $C_{15}$, or $C_5$ to $C_{10}$ aliphatic hydrocarbons. The aliphatic hydrocarbons which can be used as the organic liquid medium and/or the organic reaction medium can be cyclic or acyclic and/or can be linear or branched, unless otherwise specified. Non-limiting examples of suitable acyclic aliphatic hydrocarbon organic liquid mediums and/or organic reaction mediums that can be utilized include propane, isobutane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as the organic liquid medium and/or the organic reaction medium include cyclohexane, and methylcyclohexane. Aromatic hydrocarbons which can be used as the organic liquid medium and/or the organic reaction medium include $C_6$ to $C_{10}$ aromatic hydrocarbons. Non-limiting examples of suitable aromatic hydrocarbons that can be utilized as the organic liquid medium and/or the organic reaction medium include benzene, toluene, xylene (including ortho-xylene, meta-xylene, para-xylene, or mixtures thereof), ethylbenzene, or combinations thereof. Halogenated aliphatic hydrocarbons which can be used as the organic liquid medium and/or the organic reaction medium include $C_1$ to $C_{15}$, $C_1$ to $C_{10}$, or $C_1$ to $C_5$ halogenated aliphatic hydrocarbons. The halogenated aliphatic hydrocarbons which can be used as the organic liquid medium and/or the organic reaction medium can be cyclic or acyclic and/or can be linear or branched, unless otherwise specified. Non-limiting examples of suitable halogenated aliphatic hydrocarbons which can be utilized as the organic liquid medium and/or the organic reaction medium include methylene chloride, chloroform, carbon tetrachloride, dichloroethane, trichloroethane, and any combination thereof. Halogenated aromatic hydrocarbons which can be used as the organic liquid medium and/or the organic reaction medium include $C_6$ to $C_{20}$ or $C_6$ to $C_{10}$ halogenated aromatic hydrocarbons. Non-limiting examples of suitable halogenated aromatic hydrocarbons which can be used as the organic liquid medium and/or the organic reaction medium include chlorobenzene, dichlorobenzene, or combinations thereof.

The choice of organic liquid medium and/or organic reaction medium can be made on the basis of convenience in processing. For example, isobutane can be chosen to be compatible with the organic liquid medium and/or organic reaction medium used in processes using the product(s) of the process described herein (e.g., using the product for the formation of polymer in a subsequent processing step). In some aspects, the organic liquid medium and/or the organic reaction medium can be chosen to be easily separable from one or more of the oligomers in the oligomer product. In some aspects, an oligomer of the oligomer product can be utilized as the organic liquid medium and/or the organic reaction medium. For example, when 1-hexene is an oligomer of an ethylene trimerization process or an ethylene trimerization and tetramerization process, 1-hexene can be chosen as the organic liquid medium and/or the organic reaction medium to decrease the need for separation. When 1-octene is an oligomer of an ethylene tetramerization process or ethylene trimerization and tetramerization process, 1-octene can be chosen as the organic liquid medium and/or the organic reaction medium to decrease the need for separation.

Generally, the oligomer product that can be produced using the processes described herein can be formed at conditions (or alternatively, the reaction zone can have any conditions), which can 1) facilitate oligomer product formation, 2) provide a desired oligomer product formation rate, 3) provide acceptable catalyst system productivity, 4) provide acceptable oligomer selectivity, and/or 5) provide acceptable polymer formation. In an aspect, conditions under which the oligomer product can be formed (or alternatively, the reaction zone can have conditions that), can include one or more of catalyst system component ratios, chromium concentration, pressure, ethylene partial pressure, ethylene concentration, presence of hydrogen (and its partial pressure and/or hydrogen to ethylene mass ratio), temperature, reaction time, single pass ethylene conversion, and/or catalyst system productivity. Catalyst system component ratios, chromium concentration, pressure, ethylene partial pressure, ethylene concentration, presence of hydrogen (and its partial pressure and/or hydrogen to ethylene mass ratio), temperature, reaction time, single pass ethylene conversion, and catalyst system productivity are independently described herein and these independent descriptions can be used without limitation, and in any combination, to describe condition(s) at which the oligomer product can be formed and/or condition(s) at which the reaction zone can operate for any of the processes described herein.

In an aspect, the oligomer product can be formed (or the reaction zone can operate) at a minimum aluminum of the organoaluminum to chromium of the $N^2$-phosphinyl bicyclic amidine chromium salt complex (or alternatively, the chromium salt) molar ratio (Al to Cr molar ratio) of 10:1, 50:1, 75:1, or 100:1; alternatively or additionally, at a maximum Al to Cr molar ratio of 5,000:1, 3,000:1, 2,000:1, 1,500:1, or 1,000:1. In an aspect, the oligomer product can be formed (or the reaction zone can operate) at an Al to Cr molar ratio ranging from any minimum Al to Cr molar ratio disclosed herein to any maximum Al to Cr molar ratio disclosed herein. In a non-limiting aspect, the Al to Cr molar ratio can range from 10:1 to 5,000:1, from 50:1 to 3,000:1, from 75:1 to 2,000:1, from 100:1 to 2,000:1, or from 100:1 to 1,000:1. Other Al to Cr molar ratio ranges that can be utilized are readily apparent to those skilled in the art with the aid of this disclosure.

In an aspect, the oligomer product can be formed (or the reaction zone can operate) at a minimum reaction zone chromium of the $N^2$-phosphinyl bicyclic amidine chromium salt complex (or alternatively, the chromium of the chromium salt) concentration (i.e., minimum chromium concentration) of $1\times10^{-6}$ Cr equivalents/liter, $1\times10^{-5}$ Cr equivalents/liter, or $5\times10^{-4}$ Cr equivalents/liter; alternatively or additionally, at a maximum reaction zone chromium of the $N^2$-phosphinyl bicyclic amidine chromium salt complex (or alternatively, chromium of the chromium salt) concentration (i.e., maximum chromium concentration) of 1 Cr equivalents/liter, 0.5 Cr equivalents/liter, or 0.1 Cr equivalents/liter. In an aspect, the oligomer product can be formed (or the reaction zone can operate) at a reaction zone chromium concentration ranging from any minimum chromium concentration disclosed herein to any maximum chromium concentration disclosed herein. In a non-limiting aspect, the reaction zone chromium concentration can range from $1\times10^{-6}$ Cr equivalents/liter to 1 Cr equivalents/liter, from $1\times10^{-5}$ Cr equivalents/liter to 0.5 Cr equivalents/liter, or from $5\times10^{-4}$ Cr equivalents/liter to 0.1 Cr equivalents/liter. Other chromium concentration ranges that can be utilized are readily apparent to those skilled in the art with the aid of this disclosure.

In an aspect, the oligomer product can be formed (or the reaction zone can operate) at a minimum pressure of 5 psi (34.5 kPa), 50 psi (345 kPa), 100 psi (689 kPa), 150 psi (1.03 MPa), 250 psi (1.72 MPa), 500 psi (3.5 MPa), or 600 psi (4.1 MPa); alternatively or additionally, at a maximum pressure of 2,500 psi (17.2 MPa), 2,000 psi (13.8 MPa), 1,500 psi (10.3 MPa), 1250 psi (8.62 MPa), or 1000 psi (6.89 MPa). In an aspect, the oligomer product can be formed (or the reaction zone can operate) at a pressure ranging from any minimum pressure disclosed herein to any maximum pressure disclosed herein. In some non-limiting aspects, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (1.03 MPa) to 1500 psi (10.3 MPa), from 250 psi (1.72 MPa) to 1250 psi (8.62 MPa), from 500 psi (3.5 MPa) to 1250 psi (8.62 MPa), or from 600 psi (4.1 MPa) to 1000 psi (6.89 MPa). Other pressure ranges that can be utilized are readily apparent to those skilled in the art with the aid of this disclosure.

In an aspect, the oligomer product can be formed (or the reaction zone can operate) at a minimum ethylene partial pressure of 5 psi (34.5 kPa), 50 psi (345 kPa), 100 psi (689 kPa), 150 psi (1.03 MPa), 250 psi (1.72 MPa), or 500 psi (3.5 MPa); alternatively or additionally, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an aspect, the oligomer product can be formed (or the reaction zone can operate) at an ethylene partial pressure ranging from any minimum ethylene partial pressure disclosed herein to any maximum ethylene partial pressure disclosed herein. In some non-limiting aspects, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (1.03 MPa) to 1250 psi (8.62 MPa), from 250 psi (1.72 MPa) to 1000 psi (6.89 MPa), or from 500 psi (3.5 MPa) to 1000 psi (6.89 MPa). Other ethylene partial pressure ranges are readily apparent to those skilled in the art with the aid of this disclosure.

In an aspect, the oligomer product can be formed (or the reaction zone can operate) at a minimum ethylene concentration of 4 mass %, 10 mass %, 25 mass %, 35 mass %, or 40 mass % based upon the total mass in the reaction zone; alternatively or additionally, at a maximum ethylene concentration of 70 mass %, 65 mass %, 60 mass %, 55 mass %, 50 mass %, or 48 mass % based upon the total mass in the reaction zone. In an aspect, the oligomer product can be formed (or the reaction zone can operate) at an ethylene concentration ranging from any minimum ethylene concentration disclosed herein to any maximum ethylene concentration disclosed herein. In some non-limiting aspects, the oligomer product can be formed (or the reaction zone can operate) at an ethylene concentration in a range of from 4 mass % to 70 mass %, from 4 mass % to 65 mass %, from 10 mass % to 60 mass %, from 25 mass % to 60 mass %, from 25 mass % to 55 mass %, from 35 mass % to 50 mass %, or from 40 mass % to 48 mass % based upon the total mass in the reaction zone. Other ethylene concentration ranges that can be utilized are readily apparent to those skilled in the art with the aid of this disclosure.

In an aspect, the oligomer product can be formed (or the reaction zone can operate) at a minimum ethylene:chromium mass ratio of 50,000:1, 150,000:1, 250,000:1, or 400,000:1; alternatively, or additionally, at a maximum ethylene:chromium mass ratio of 5,000,000:1, 2,500,000:1, 1,500,000:1, or 1,000,000:1. In an aspect, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting aspects, the oligomer product can be formed (or the reaction zone can operate) at an ethylene:chromium mass ratio in the range of 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure. Generally, the ethylene:chromium mass ratio is based upon the chromium in the $N^2$-phosphinyl bicyclic amidine chromium salt complex (or alternatively, the chromium salt).

In an aspect wherein hydrogen is utilized, the oligomer product can be formed (or the reaction zone can operate) at a minimum hydrogen partial pressure of 1 psi (6.9 kPa), 2 psi (14 kPa), 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psi (517 kPa), or 50 psi (345 kPa). In an aspect, the oligomer product can be formed (or the reaction zone can operate) at a hydrogen partial pressure ranging from any minimum hydrogen partial pressure disclosed herein to any maximum hydrogen partial pressure disclosed herein. In some non-limiting aspects, wherein hydrogen is utilized, the oligomer product can be formed (or the reaction zone can operate) at a hydrogen partial pressure from 1 psi (6.9 kPa) to 200 psi (1.4 MPa), from 2 psi (14 kPa) to 150 psi (1.03 MPa), from 5 psi (34 kPa) to 100 psi (689 kPa), from 10 psi (69 kPa) to 75 psi (517 kPa), or from 15 psi (103 kPa) to 50 psi (345 kPa). Other hydrogen partial pressure ranges that can be utilized are readily apparent to those skilled in the art with the aid of this disclosure.

In an aspect wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio of (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an aspect, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting aspects, the oligomer product can be formed (or the reaction zone can operate) at a hydrogen to ethylene mass ratio from (0.05 g hydrogen)/(kg ethylene) to (5 g hydrogen)/(kg ethylene), from (0.1 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), from (0.5 g hydrogen)/(kg ethylene) to (2 g hydrogen)/(kg ethylene), or from (0.5 g hydrogen)/(kg ethylene) to (1.5 g hydrogen)/(kg ethylene). Other hydrogen to ethylene mass ratio ranges that can be utilized are readily apparent to those skilled in the art with the aid of this disclosure.

In an aspect, the oligomer product can be formed (or the reaction zone can operate) at a minimum hydrogen:chromium of the $N^2$-phosphinyl bicyclic amidine chromium salt complex (or alternatively, the chromium salt) mass ratio (minimum hydrogen:chromium mass ratio) of 1:1, 50:1, 100:1, or 200:1; alternatively or additionally, at a maximum hydrogen:chromium of the $N^2$-phosphinyl bicyclic amidine chromium salt complex (or alternatively, the chromium salt) mass ratio (maximum hydrogen:chromium mass ratio) of 100,000:1, 50,000:1, 10,000:1, or 3,000:1. In an aspect, the oligomer product can be formed (or the reaction zone can operate) at a hydrogen:chromium of the $N^2$-phosphinyl bicyclic amidine chromium salt complex (or alternatively, the chromium salt) mass ratio (hydrogen:chromium mass ratio) ranging from any minimum hydrogen:chromium mass ratio disclosed herein to any maximum hydrogen:chromium mass ratio disclosed herein. In some non-limiting aspects, the oligomer product can be formed (or the reaction zone can operate) at a hydrogen:chromium mass ratio in the range of 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure. Generally, the hydrogen:chromium mass ratio is based upon the chromium in the $N^2$-phosphinyl bicyclic amidine chromium salt complex (or alternatively, the chromium salt).

In an aspect, the oligomer product can be formed (or the reaction zone can operate) at a minimum temperature of 0° C., 25° C., 40° C., or 50° C.; alternatively, or additionally, at a maximum temperature of 200° C., 150° C., 100° C., or 90° C. In an aspect, the oligomer product can be formed (or the reaction zone can operate) at a temperature ranging from any minimum temperature disclosed herein to any maximum temperature disclosed herein. In some non-limiting aspects, the oligomer product can be formed (or the reaction zone can operate) at a temperature from 0° C. to 200° C., from 25° C. to 150° C., from 40° C. to 100° C., from 50° C. to 100° C., or from 50° C. to 90° C. Other temperature ranges that can be utilized are readily apparent to those skilled in the art with the aid of this disclosure.

The reaction time (or residence time or average residence time) in the reaction zone can comprise any time that can produce the desired quantity of oligomer product; alternatively, any reaction time (or residence time) that can provide a desired catalyst system productivity; alternatively, any reaction time (or residence time or average residence time) that can provide a desired ethylene conversion. Relating to forming the oligomer product, the oligomer product can be formed over a period of time (or an average residence time) that can produce the desired quantity of olefin product or polymer product, provide the desired catalyst system productivity, and/or provide the desired conversion of monomer. In some aspects, the reaction time (or residence time or average residence time) can range from 1 minute to 5 hours; alternatively, can range from 5 minutes to 2.5 hours; alternatively, can range from 10 minutes to 2 hours; or alternatively, can range from 15 minutes to 1.5 hours. In some aspects (in continuous process aspects), the reaction time (or residence time or average residence time) can be stated as an average reaction time (or average residence time) and can range from 1 minute to 5 hours; alternatively, can range from 5 minutes to 2.5 hours; alternatively, can range from 10 minutes to 2 hours; or alternatively, can range from 15 minutes to 1.5 hours.

In an aspect, the processes described herein can have an ethylene conversion of at least 30%, 35%, 40%, or 45%. In another aspect, the ethylene conversion can be a single pass conversion of at least 30%, 35%, 40%, or 45%.

In an aspect, the processes described herein can have a catalyst system productivity of greater than 10,000 grams, 50,000 grams, 100,000 grams, 150,000 grams, 200,000 grams, 300,000 grams, or 400,000 grams ($C_6+C_8$) per gram of chromium (g ($C_6+C_8$)/g Cr).

Depending upon the catalyst system utilized, the processes described herein can be an ethylene oligomerization process, an ethylene trimerization process, an ethylene tetramerization process, or an ethylene trimerization and tetramerization process; alternatively, an ethylene oligomerization process; alternatively, an ethylene trimerization process; alternatively, an ethylene tetramerization process; or alternatively an ethylene trimerization and tetramerization process. In ethylene trimerization aspects, the oligomer product can comprise at least 70 wt. % hexenes, at least 75 wt. % hexenes, at least 80 wt. % hexenes, at least 85 wt. % hexenes, or at least 90 wt. % hexenes based upon the weight of the oligomer product. In some ethylene trimerization aspects, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In ethylene tetramerization aspects, the oligomer product can comprise at least 70 wt. % octenes, at least 75 wt. % octenes, at least 80 wt. % octenes, at least 85 wt. % octenes, or at least 90 wt. % octenes based upon the weight of the oligomer product. In some ethylene tetramerization aspects, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In ethylene trimerization and tetramerization aspects, the oligomer product can comprise at least 70 wt. % hexenes and octenes, at least 75 wt. % hexenes and octenes, at least 80 wt. % hexenes and octenes, at least 85 wt. % hexenes and octenes, or at least 90 wt. % hexenes and octenes based upon the weight of the oligomer product. In some ethylene trimerization and tetramerization aspects, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization aspects, the ethylene trimer can comprise at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer. In other ethylene oligomerization, ethylene trimerization, or ethylene trimerization and tetramerization aspects, the ethylene trimer can comprise from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization aspects, the ethylene tetramer can comprise at least 85 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively, at least 98 wt. % 1-octene by weight of the ethylene tetramer. In other ethylene oligomerization, ethylene tetramerization, or ethylene trimerization and tetramerization aspects, the ethylene tetramer can comprise from 85 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

In some aspects, the processes described herein utilizing the $N^2$-phosphinyl bicyclic amidine chromium salt complex (or alternatively, the $N^2$-phosphinyl bicyclic amidine and the chromium salt) can produce an oligomer product comprising a mixture of $C_8$ and $C_6$ olefin products wherein the mass ratio of $C_8$ olefin products to $C_6$ olefin products can be at least 0.5:1, at least 1:1, at least 1.5:1, or at least 1.75:1.

EXAMPLES

Methodology

Development of accurate density-functional theory (DFT), solvation methods, and quantum mechanical tools have emerged that can enable prediction of products from molecular catalysts. One area of interest is to be able to predict the relative amounts of hexenes and/or octenes produced by an ethylene trimerization and/or tetramerization catalyst system. To be able to use computational methods to predict the relative amounts of hexenes and/or octenes produced by a particular ethylene trimerization and/or tetramerization catalyst, a plausible mechanism capable of demonstrating hexenes and/or octenes selectivity is needed. Using computational and experimental studies of i) Britovsek, G. J. P. and McGuinness, D. S. Chem. Eur. J. 2016, 22, 16891-16896, ii) Britovsek, G. J. P.; McGuinness, D. S.; Tomov, A. K. Catal. Sci. Technol. 2016, 6, 8234-8241, iii) Hossain, M. A.; Kim, H. S.; Houk, K. N. Cheong, M. Bull.

Korean Chem. Soc. 2014, 35, 2835-2838, iv) Gong, M.; Liu, Z.; Li, Y.; Ma, Y.; Sun, Q.; Zhang, J.; Liu, B. Organometallics 2016, 35, 972-981, v) Yang, Y.; Liu, Z.; Cheng, R.; He, X.; Liu, B. Organometallics 2014, 33, 2599-2607, vi) Qi, Y.; Zhong, L.; Liu, Z.; Qiu, P.; Cheng, R.; He, X.; Vanderbilt, J.; Liu, B. Organometallics 2010, 29, 1588-1602, vii) Budzelaar, P. H. M. Can. J. Chem. 2009, 87, 832-837, viii) Bhaduri, S.; Mukhopadhyay, S.; Kulkarni, S. A. J. Organomet. Chem. 2009, 694, 1297-1307, and ix) van Rensburg, W. J.; Grove, C.; Steynberg, J. P.; Stark, K. B.; Huyser, J. J.; Steynberg, P. J. Organometallics 2004, 23, 1207-1222, and experimental studies of Bartlett, S. A.; Moulin, J.; Tromp, M.; Reid, G.; Dent, A. J.; Cibin, G.; McGuinness, D. S.; Evans, J. ACS Catal. 2014, 4, 4201-4204, and without being limited by theory, Scheme 1 was developed as a plausible catalytic mechanism for ethylene trimerization and/or tetramerization.

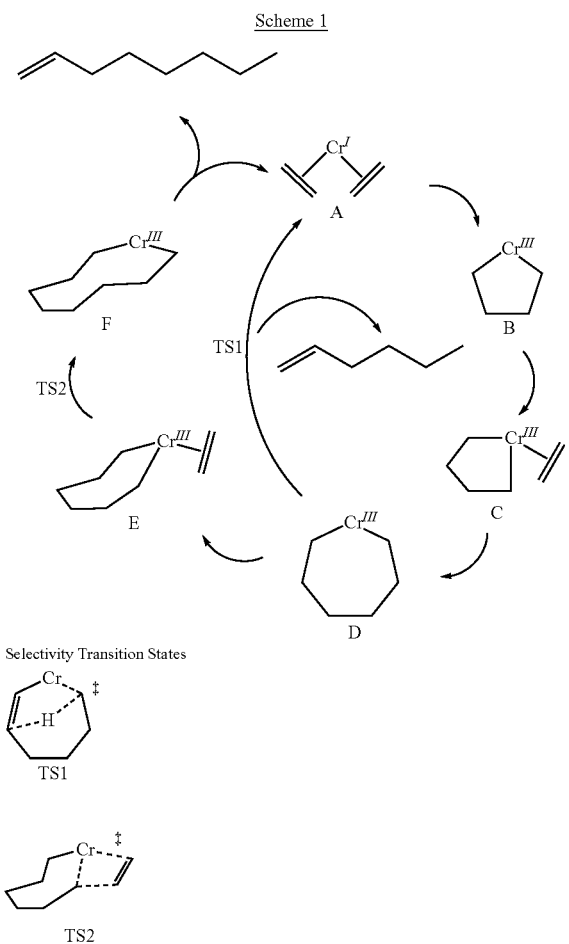

Scheme 1

Selectivity Transition States

TS1

TS2

In Scheme 1, precatalyst activation in the presence of ethylene can generate a low-valent Cr ethylene coordination species A. Oxidative C—C bond coupling of the two ethylene units can form chromacyclopentane B which can then coordinate with another ethylene to form the chromacyclopentane ethylene coordination species C followed by migratory ethylene insertion which can lead to the chromacycloheptane intermediate D. Intermediate D represents the common intermediate in the mechanistic paths where the mechanisms for producing hexenes and octenes can diverge. Hexenes can be produced from the chromacycloheptane intermediate D by β-hydrogen transfer via transition state TS1 to form 1-hexene and a reduced Cr species which can then reform, in the presence of ethylene, the low-valent Cr ethylene coordination species A. Octenes can be produced from the chromacycloheptane intermediate D by i) ethylene coordination to form the ethylene coordinated species E, ii) migratory insertion of ethylene through transition state TS2 to form the chromacyclononane species F, and iii) β-hydrogen transfer within chromacyclononane species F to produce 1-octene and a reduced Cr species which can then reform, in the presence of ethylene, the low-valent Cr ethylene coordination species A. This two-transition state model assumes dynamic equilibrium, often known as Curtin-Hammett conditions, where TS1 and TS2 arise from the common chromacycloheptane intermediate D and a fast equilibrium of possible intermediates leading up to TS1 and TS2. Via this mechanism selectivity can result from competitive β-hydrogen transfer of transition state TS1 and the migratory ethylene insertion from intermediate D through transition state TS2.

Without being limited by theory, the mechanism in Scheme 1 was then applied in a predictive method to allow for prediction of the relative amounts of hexenes and/or octenes for previously unknown heteroatomic ligand chromium salt complexes; for example, the herein disclosed $N^2$-phosphinyl bicyclic amidine chromium salt complexes. In this predictive method, Density Functional Theory calculations were applied to experimentally evaluated $N^2$-phosphinyl amidine chromium salt complexes to provide a correlation between the Density Functional Theory calculations and the experimentally observed amounts of hexenes and/or octenes. The correlation was then used to predict the amounts of hexenes and/or octenes produced by the herein disclosed $N^2$-phosphinyl bicyclic amidine chromium salt complexes.

Without wishing to be limited by theory, Scheme 2 and Scheme 3 illustrates the critical competing and selectivity determining reaction coordinate pathways for producing hexenes and octenes using $N^2$-phosphinyl bicyclic amidine chromium salt complexes having Structure NPBACr I or Structure NPBACr II, respectively. These schemes include the respective general $N^2$-phosphinyl bicyclic amidine chromium salt complex CrCH 1, the respective general $N^2$-phosphinyl bicyclic amidine chromium salt complex CrCH 2, the respective general $N^2$-phosphinyl bicyclic amidine chromium salt complex hexene transition state TS C6, and the respective general $N^2$-phosphinyl bicyclic amidine chromium salt complex octene transition state TS C8. Thus, for catalyst systems based upon general $N^2$-phosphinyl bicyclic amidine chromium salt complexes having Structure NPBACr I or Structure NPBACr II, the Gibbs free energy difference, $\Delta\Delta G^\ddagger$, between: 1) the difference in the Gibbs free energy of the respective general $N^2$-phosphinyl bicyclic amidine chromium chromacycloheptane complex CrCH 1 and the respective general $N^2$-phosphinyl bicyclic amidine chromium salt complex hexene transition state TS C6; and 2) the difference in the Gibbs free energy of the respective general $N^2$-phosphinyl bicyclic amidine chromium chromacycloheptane complex CrCH 2 and the respective general $N^2$-phosphinyl bicyclic amidine chromium salt complex octene transition state TS C8 can be utilized in a predictive correlative method to predict the relative amounts of hexenes and/or octenes produced by an $N^2$-phosphinyl bicyclic amidine chromium salt complex NPBACr I or Structure NPBACr II. Further, and without being limited by theory, since the respective general $N^2$-phosphinyl bicyclic amidine chromium chromacycloheptane complex CrCH 1 and the general N²-phosphinyl amidine chromium chromacycloheptane complex CrCH 2 are carbon-carbon chromacycloheptane rotational isomers of each other and it is expected that there is a low energy barrier for their interconversion, the calculation of the Gibbs free energy difference, $\Delta\Delta G^\ddagger$, can be simplified to the calculation of the Gibbs free energy difference between the respective general N²-phosphinyl bicyclic amidine chromium salt complex hexene transition state TS C6 and the respective general N²-phosphinyl bicyclic amidine chromium salt complex octene transition state TS C8 ($\Delta\Delta G^\ddagger$, in Scheme 2). Thus, the Gibbs free energy difference $\Delta\Delta G^\ddagger$ was correlated with the experimentally observed amounts of hexenes and/or octenes produced by the experimentally tested N²-phosphinyl bicyclic amidine chromium salt complexes.

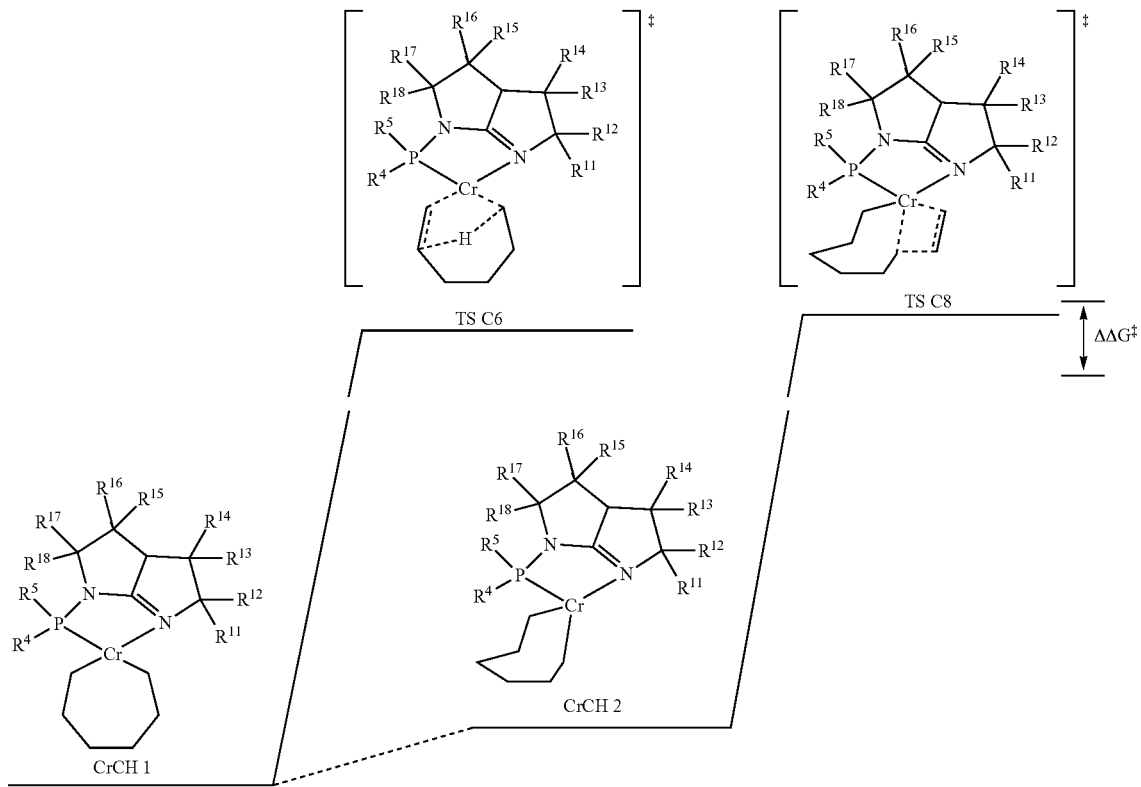

Scheme 2

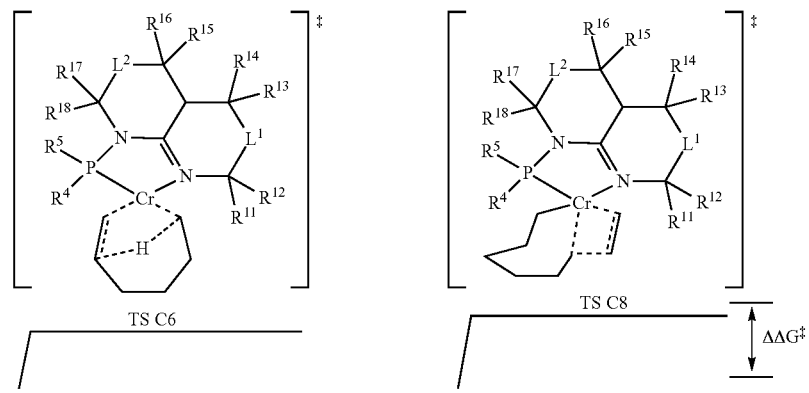

Scheme 3

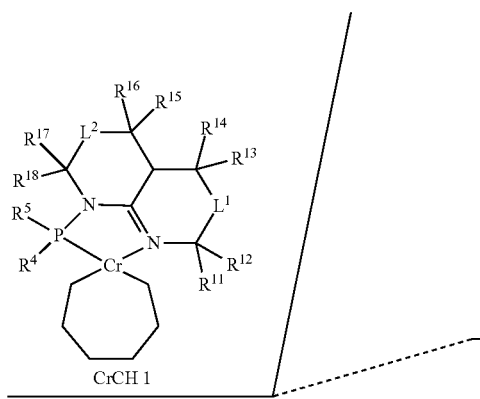
CrCH 1

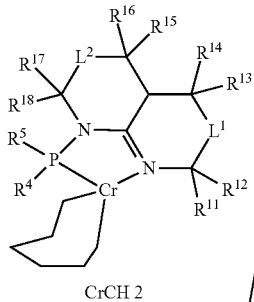
CrCH 2

Density Functional Theory Calculations

Density Functional Theory calculations (specifically, unrestricted UMO6L/Def2-TZVP//UM06/6-31G(d,p) (LANL2DZ) theory) combined with the SMD implicit solvent model for cyclohexane (as implemented in Marenich, A. V.; Cramer, C. J.; Truhlar, D. G., *J. Phys. Chem. B.* 2009, 113, 6378-6396) was used to calculate the Gibbs free energy of the cationic $N^2$-phosphinyl bicyclic amidine chromium salt complex hexene transition state TS C6 (hereafter $N^2$-phosphinyl bicyclic amidine chromium salt complex hexene transition state TS C6) and the cationic $N^2$-phosphinyl bicyclic amidine chromium salt complex octene transition state TS C8 (hereafter $N^2$-phosphinyl bicyclic amidine chromium salt complex hexene transition state TS C8) and, for each $N^2$-phosphinyl bicyclic amidine chromium salt complex. The Gibbs free energy difference between the $N^2$-phosphinyl bicyclic amidine chromium salt complex hexene transition state TS C6 and the $N^2$-phosphinyl bicyclic amidine chromium salt complex octene transition state TS C8, $\Delta\Delta G^{\ddagger}$, for each $N^2$-phosphinyl bicyclic amidine chromium salt complex was then calculated. The calculations of the Gibbs free energy of the cationic $N^2$-phosphinyl bicyclic amidine chromium salt complex transition state TS C6 (and other transition state energies used herein) and the cationic $N^2$-phosphinyl bicyclic amidine chromium salt complex octene transition state TS C8 (and other transition state energies used herein) were performed without considering the impact of the balancing anion.

The density functional theory calculations were carried out using Gaussian 09 (Frisch, M. J. et al. *Gaussian 09™, Revision B*.01, Gaussian, Inc.: Wallingford, Conn., USA, 2009).

Geometries to account for each degree of freedom and each spin state for the $N^2$-phosphinyl bicyclic amidine chromium salt complex hexene transition state TS C6 (3 to 40 conformations depending on the exact ligand) and the $N^2$-phosphinyl bicyclic amidine chromium salt complex octene transition state TS C8 (3 to 40 conformation depending on the exact ligand) for each $N^2$-phosphinyl bicyclic amidine chromium salt complex were calculated using the pseudopotential LANL2DZ basis set for chromium (integrated into the *Gaussian 09™, Revision B*.01) and the unrestricted approximation of local Minnesota 06 density functional theory 6-31G(d,p) basis set (i.e., UM06/6-31G(d, p) basis set) for all other atoms in the $N^2$-phosphinyl bicyclic amidine chromium salt transition states. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure. Additionally, zero point energies ($\Delta E_{ZPE(small)}$), vibrational, rotational, and translational energies ($\Delta U_{vib(small)}$, $\Delta U_{rot(small)}$, $\Delta U_{trans(small)}$, respectively), and vibrational, rotational, and translational entropies ($\Delta S_{vib(small)}$, $\Delta S_{rot(small)}$, $\Delta S_{trans(small)}$, respectively) were obtained to use in the calculation of the Gibbs free energy for the $N^2$-phosphinyl bicyclic amidine chromium salt complex hexene transition state TS C6 and the $N^2$-phosphinyl bicyclic amidine chromium salt complex octene transition state TS C8.

The solvated geometries for the $N^2$-phosphinyl bicyclic amidine chromium salt complex hexene transition state TS C6 conformation having the lowest energy and the $N^2$-phosphinyl bicyclic amidine chromium salt complex octene transition state TS C8 conformation having the lowest energy, along with any conformations having an energy relatively close to the $N^2$-phosphinyl bicyclic amidine chromium salt complex hexene transition state TS C6 conformation having the lowest energy and the $N^2$-phosphinyl bicyclic amidine chromium salt complex octene transition state TS C8 conformation having the lowest energy, were calculated using a continuum model (SMD) that was parametrized and implemented in Gaussian 09 for cyclohexane. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure.

The total self-consistent field electronic energy containing the electron kinetic and potential energies, and nuclear repulsion energy ($E_{(large)}$) and the standard state solvation free energy change ($\Delta G_{solv(large)}$) for the $N^2$-phosphinyl bicyclic amidine chromium salt complex hexene transition state TS C6 and the $N^2$-phosphinyl bicyclic amidine chromium salt complex octene transition state TS C8 were then calculated using the unrestricted approximation of local Minnesota 06 density functional theory Def2-TZVP basis set UMO6L/Def2-TZVP (downloaded from https://bse.pnl-.gov/bse/portal on Jan. 1, 2016) to provide accurate spin state energies and accurate calculations for weak dispersion forces.

The Gibbs free energy of the N²-phosphinyl bicyclic amidine chromium salt complex hexene transition state TS C6 and the N²-phosphinyl bicyclic amidine chromium salt complex octene transition state TS C8 were then calculated using the equation $E_{(large)} + \Delta E_{ZPE(small)} + \Delta U_{vib(small)} + \Delta U_{rot(small)} + \Delta U_{trans(small)} + nRT - T\Delta S_{vib(small)} - T\Delta S_{rot(small)} - T\Delta S_{trans(small)} + \Delta G_{solv(large)}$ where R is the ideal gas constant and T is the temperature (298 K was used for these calculations). The Gibbs free energy difference, $\Delta\Delta G^{\ddagger}$, between the N²-phosphinyl bicyclic amidine chromium salt complex hexene transition state TS C6 and the N²-phosphinyl bicyclic amidine chromium salt complex octene transition state TS C8 for each N²-phosphinyl bicyclic amidine chromium salt complex was then calculated as the Gibbs free energy of N²-phosphinyl bicyclic amidine chromium salt complex hexene transition state TS C6 minus the Gibbs free energy of the N²-phosphinyl bicyclic amidine chromium salt complex octene transition state TS C8.

Table 1 provides the calculated $\Delta\Delta G^{\ddagger}$ values between N²-phosphinyl amidine chromium salt complex hexene transition state TS C6 and N²-phosphinyl amidine chromium salt complex octene transition state TS C8 for five N²-phosphinyl amidine chromium salt complexes (NPA 1-NPA 5) for which experimental data using a chromium complex having the indicated N²-phosphinyl amidine ligand had been determined (see Ethylene Oligomerization Examples). Table 1 further provides predictive values of $\Delta\Delta G^{\ddagger}$ and product distribution for N²-phosphinyl bicyclic amidine chromium salt complexes using the ligand having Structure NPBA 1, NPBA 2, and NPBA3.

Ethylene Oligomerizations Examples

A 1L stainless steel autoclave reactor was dried under vacuum at 110° C. for at least 8 hours prior to use. The reactor was then cooled to 50° C. In a drybox, a 20 mL glass vial was charged with an N²-phosphinyl amidine chromium complex (0.009-0.010 mmol), ethylbenzene (2.00 g), MMAO-3A (400-800 equivalents), Al (7 wt. % Al solution in heptanes), and an internal standard (n-nonane, 1.00 g). This solution was then added to a 0.5 L glass charger containing cyclohexane (400 mL). The combined solution was removed from the drybox and charged into the 1 L stainless steel autoclave reactor under static vacuum. The reactor was then heated to 5° C. below the reaction temperature and charged with hydrogen. Ethylene was then charged to the reactor on-demand to maintain the desired operating pressure. After 30 minutes, water cooling was applied to the 1L stainless steel autoclave reactor to terminate the ethylene oligomerization reaction. When the reactor temperature reached 35° C., the unreacted ethylene and hydrogen gas was vented to the atmosphere. A liquid sample of the 1L stainless steel autoclave reactor contents was then collected at room temperature and analyzed by gas chromatography. The reactor solids were collected by filtering the reaction and cleaning the reactor walls and cooling coil. The mass % of the trimer (1-hexene) and tetramer (1-octene) observed in the oligomer product (as a percentage of the total trimer and tetramer produced) for each of chromium salt complexes of N²-phosphinyl amidine ligands 1-5 are reported in Table 1.

TABLE 1

| Ligand† | Calculated Values | | | | Experimentally Observed Values | |
|---|---|---|---|---|---|---|
| | $\Delta\Delta G^{\ddagger}$, kcal | Trimer, mass % | Tetramer, mass % | P—Cr—N Bond Angle, ° | Trimer, mass % | Tetramer, mass % |
| 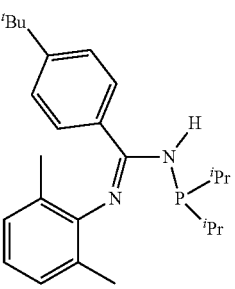 [SMILES: Cc1cccc(C)c1/N=C(/NP(C(C)C)C(C)C)c1ccc(C(C)(C)C)cc1] | 2.4 | 99.1 | 0.9 | 77 | 93.6 | 0.9 |
| 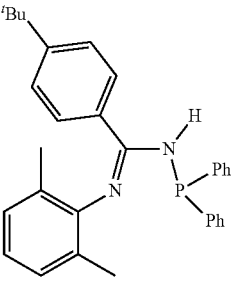 [SMILES: Cc1cccc(C)c1/N=C(/NP(c1ccccc1)c1ccccc1)c1ccc(C(C)(C)C)cc1] | −0.5 | 82.6 | 17.4 | 76 | 85.4 | 12 |

TABLE 1-continued
| Ligand† | Calculated Values | | | | Experimentally Observed Values | |
|---|---|---|---|---|---|---|
| | ΔΔG‡, kcal | Trimer, mass % | Tetramer, mass % | P—Cr—N Bond Angle, ° | Trimer, mass % | Tetramer, mass % |
| 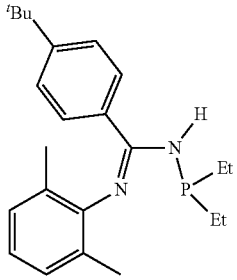 [SMILES: CCP(CC)N/C(=N/c1c(C)cccc1C)c1ccc(C(C)(C)C)cc1] | −0.2 | 86.9 | 13.1 | 75 | 79.3 | 15 |
| 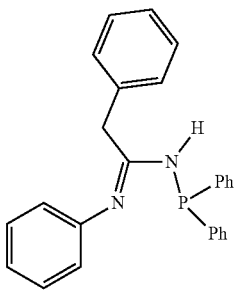 [SMILES: c1ccc(C/C(=N\c2ccccc2)NP(c2ccccc2)c2ccccc2)cc1] | −1.3 | 65.9 | 34.1 | 76 | 65.2 | 30.5 |
| 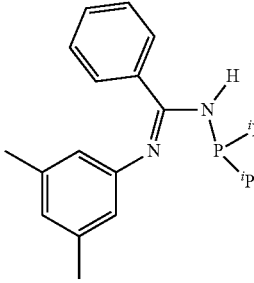 | −1.3 | 66.9 | 33.1 | 77 | 52.2 | 33.7 |
| 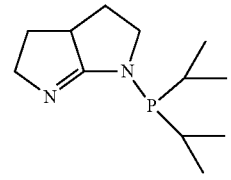 | −3.23 | 20.3 | 79.7 | 78.7/78.5 | ND | ND |
| 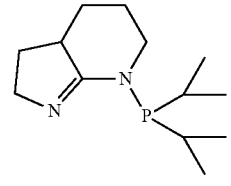 | −1.46 | 63.4 | 36.6 | 77.2/76.8 | ND | ND |
| 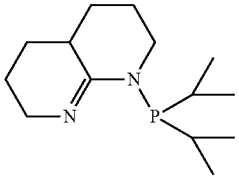 | 3.61 | 99.8 | 0.02 | 77.2/75.2 | ND | ND |
†$^t$Bu = tert-butyl, $^i$Pr = isopropyl, Ph = phenyl, Et = ethyl Correlation of $\Delta\Delta G^{\ddagger}$ and $C_6/C_8$ Mass Ratio The calculated $\Delta\Delta G^{\ddagger}$ for the experimentally evaluated chromium salt complexes of the $N^2$-phosphinyl amidine ligands NPA 1-NPA 5 were found to provide a good linear correlation with the natural logarithm of the $C_6$ to $C_8$ mass ratio, ln(mass $C_6$/mass $C_8$) (or alternatively ln($C_6/C_8$), observed when the chromium salt complexes of the five $N^2$-phosphinyl amidine ligands were utilized in a catalyst system for oligomerizing ethylene (see Ethylene Oligomerization Examples provided herein). FIG. 1 provides a graph of the calculated $\Delta\Delta G^{\ddagger}$ versus ln($C_6/C_8$) for the chromium salt complexes of the five $N^2$-phosphinyl amidine ligands in Table 1. The least squares fitted line of this data had a correlation coefficient, $R^2$, of 0.9744 indicating a good correlation between $\Delta\Delta G^{\ddagger}$ and the experimentally observed mass of hexenes and octenes. Use of the $\Delta\Delta G^{\ddagger}$ versus ln($C_6/C_5$) trend line to calculate the ln($C_6/C_5$) for the chromium salt complex of the $N^2$-phosphinyl bicyclic amidine ligands having structures NPBA 1-NPBA 3. The linear correlation provide in FIG. 1 was then utilized to determine the ln($C_6/C_8$) and the corresponding mass % $C_6$ and mass % of $C_8$ provided in Table 1.

Synthesis of $N^2$-phosphinyl Amidine Ligands

The synthesis of the $N^2$-phosphinyl amidine ligands (NPA 1-NPA 5) was, and the potential synthesis of the $N^2$-phosphinyl bicyclic amidine ligands of the present disclosure (e.g., NPBA 1, NPBA 2, and NPBA 3) can be performed using the general synthetic procedures as provided in U.S. patent application Ser. No. 15/166,991 and U.S. patent application Ser. No. 15/171,170 which are incorporated herein by reference in their entirety.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the detailed description of the present disclosure. The disclosures of all patents, patent applications, and publications cited herein are hereby incorporated by reference.

Statement 1. A catalyst system comprising i) (a) an $N^2$-phosphinyl bicyclic amidine chromium salt complex having Structure NPBACr I or Structure NPBACr II

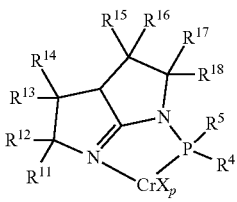

NPBACr I

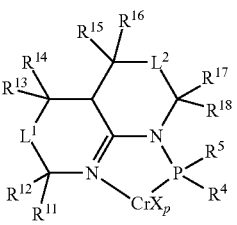

NPBACr II or (b) a chromium salt and an $N^2$-phosphinyl bicyclic amidine having Structure NPBA I or Structure NPBA II

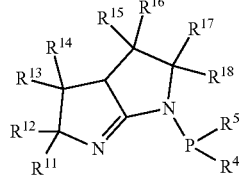

NPBA I

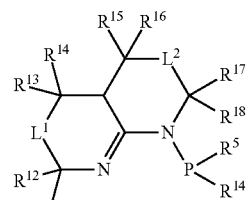

NPBA II wherein $R^{11}$, $R^{12}$, $R^{13}$, $R^{14}$, $R^{15}$, $R^{16}$, $R^{17}$, and $R^{18}$ independently are a hydrogen or a $C_1$ to $C_{30}$ organyl group, $L^1$ and $L^2$ independently are a $C_1$ to $C_{30}$ a hydrocarbylene group, $R^4$ and $R^5$ independently are a $C_1$ to $C_{30}$ organyl group and $R^4$ and $R^5$ optionally are combined to form $L^{45}$ forming a ring or ring system including the phosphorus atom where $L^{45}$ is a $C_1$ to $C_{30}$ organylene group, $CrX_p$ is a chromium salt where X is a monoanion and p is an integer from 2 to 6; and ii) an organoaluminum compound.

Statement 2. The catalyst system of statement 1, wherein the organoaluminum compound comprises an aluminoxane.

Statement 3. The catalyst system of statement 2, wherein the aluminoxane comprises methylaluminoxane (MAO), a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

Statement 4. The catalyst system of any one of statements 1 to 3, where the catalyst system has an aluminum of the organoaluminum compound to chromium of the chromium salt or chromium of the $N^2$-phosphinyl bicyclic amidine chromium salt complex molar ratio in the range of 10:1 to 5,000:1.

Statement 5. A process comprising: a) contacting i) ethylene, ii) a catalyst system comprising (a) (i) an $N^2$-phosphinyl bicyclic amidine chromium salt complex having Structure NPBACr I or Structure NPBACr II

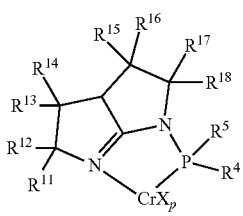

NPBACr I

-continued

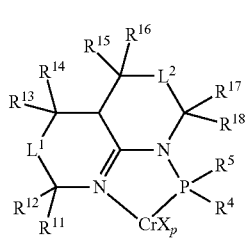

NPBACr II or (ii) an $N^2$-phosphinyl bicyclic amidine having Structure NPBA I or Structure NPBA II

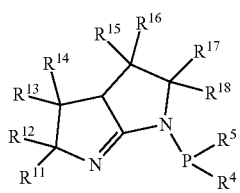

NPBA I

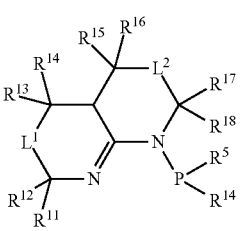

NPBA II wherein $R^{11}$, $R^{12}$, $R^{13}$, $R^{14}$, $R^{15}$, $R^{16}$, $R^{17}$, and $R^{18}$ independently are a hydrogen or a $C_1$ to $C_{30}$ organyl group, $L^1$ and $L^2$ independently are a $C_1$ to $C_{30}$ a hydrocarbylene group, $R^4$ and $R^5$ independently are a $C_1$ to $C_{30}$ organyl group and $R^4$ and $R^5$ optionally are combined to form $L^{45}$ forming a ring or ring system including the phosphorus atom where $L^{45}$ is a $C_1$ to $C_{30}$ organylene group, $CrX_p$ is a chromium salt where X is a monoanion and p is an integer from 2 to 6, and (b) an organoaluminum compound, and iii) optionally an organic reaction medium; and b) forming an oligomer product in a reaction zone.

Statement 6. The process of statement 5, wherein the reaction zone has any temperature disclosed herein (e.g., at least 0° C., 25° C., 40° C., or 50° C., in a range of 0° C. to 200° C., 25° C. to 150° C., 40° C. to 100° C., 50° C. to 100° C., or 50° C. to 90° C., among others).

Statement 7. The process of any one of statements 5 or 6, wherein the reaction zone has any ethylene partial pressure disclosed herein (e.g., at least 5 psi (34.5 kPa), 50 psi (345 kPa), 250 psi (1.72 MPa), or 500 psi (3.5 MPa), in the range of 5 psi (34.5 kPa) to 2,500 psi (17.2 MPa), from 5 psi (34.5 kPa) to 2,000 psi (13.8 MPa), from 100 psi (689 kPa) to 2,000 psi (13.8 MPa), from 500 psi (3.5 MPa) to 1500 psi (10.3 MPa), from 150 psi (1.03 MPa) to 1250 psi (8.62 MPa), or from 250 psi (1.72 MPa) to 1000 psi (6.89 MPa), among others).

Statement 8. The process of any one of statements 5 to 7, wherein the reaction zone has any ethylene:chromium mass ratio disclosed herein (e.g., 50,000:1, 150,000:1, 250,000:1, or 400,000:1, in the range of 50,000:1 to 5,000,000:1, 150,000:1 to 2,500,000:1, 250,000:1 to 1,500,000:1, or 400,000:1 to 1,000,000:1, among others).

Statement 9. The process of Statement 8, wherein the organoaluminum compound comprises, or consists essentially of, an aluminoxane.

Statement 10. The process of Statement 9, wherein the aluminoxane comprises, or consists essentially of, methylaluminoxane (MAO), a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentyl-aluminoxane, iso-pentylaluminoxane, neopentylaluminoxane, or mixtures thereof.

Statement 11. The process of any one of statements 5 to 10, wherein the reaction zone has any aluminum of the organoaluminum compound to chromium of the $N^2$-phosphinyl bicyclic amidine chromium salt complex molar ratio disclosed herein (e.g., at least 10:1, 50:1, 75:1, or 100:1, in the range of 10:1 to 5,000:1, from 50:1 to 3,000:1, from 50:1 to 3,000:1, from 75:1 to 2,000:1, from 100:1 to 2,000:1, of from 100:1 to 1,000:1, among others).

Statement 12. The process of any one of statements 5 to 11, wherein the reaction zone has any chromium of the $N^2$-phosphinyl bicyclic amidine chromium salt complex concentration disclosed herein (e.g., at least $1 \times 10^{-6}$ Cr equivalents/liter, $1 \times 10^{-5}$ Cr equivalents/liter, or $5 \times 10^{-4}$ Cr equivalents/liter, in the range of $1 \times 10^{-6}$ Cr equivalents/liter to 1 Cr equivalents/liter, $1 \times 10^{-5}$ Cr equivalents/liter to $5 \times 10^{-1}$ Cr equivalents/liter, $5 \times 10^{-4}$ Cr equivalents/liter to $1 \times 10^{-1}$ Cr equivalents/liter, among others).

Statement 13. The process of any one of statements 5 to 12, wherein the reaction zone has any ethylene concentration disclosed herein (e.g., at least 4 mass %, 10 mass %, 25 mass %, 35 mass %, or 40 mass %, in the range of 4 mass % to 70 mass %, from 4 mass % to 60 mass %, from 10 mass % to 60 mass %, from 25 mass % to 55 mass %, 35 mass % to 50 mass %, or 40 mass % to 48 mass %, among others) based upon the total mass in the reaction zone.

Statement 14. The process of any one of statements 5 to 13, wherein the process further comprises contacting hydrogen with the ethylene, the catalyst system, and the optional organic reaction medium and the reaction zone has any hydrogen partial pressure disclosed herein (e.g., at least 1 psi (6.9 kPa), 2 psi (14 kPa), 5 psi (34 kPa), 10 psi (69 kPa), or 15 psi (103 kPa), in the range of 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa), among others).

Statement 15. The process of any one of statements 5 to 13, wherein the process further comprises contacting hydrogen with the ethylene, the catalyst system, and the optional organic reaction medium and the reaction zone has any hydrogen to ethylene mass ratio disclosed herein (e.g., at least (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene), in the range of (0.05 g hydrogen)/(kg ethylene) to (5 g hydrogen)/(kg ethylene), from (0.25 g hydrogen)/(kg ethylene) to (5 g hydrogen)/(kg ethylene), (0.25 g hydrogen)/(kg ethylene) to (4 g hydrogen)/(kg ethylene), (0.4 g hydrogen)/(kg ethylene) to (3 g hydrogen)/(kg ethylene), (0.4 g hydrogen)/(kg ethylene) to (2.5 g hydrogen)/(kg ethylene), (0.4 g hydrogen)/(kg ethylene) to (2 g hydrogen)/(kg ethylene), or (0.5 g hydrogen)/(kg ethylene) to (2 g hydrogen)/(kg ethylene), among others).

Statement 16. The process of statement 14 or 15, wherein the process further comprises contacting hydrogen with the ethylene, the catalyst system, and the optional organic reaction medium and the reaction zone has any hydrogen: chromium mass ratio disclosed herein (e.g., at least 1:1, 50:1, 100:1, or 200:1, in the range of 1:1 to 100,000:1, 50:1 to 50,000:1, 100:1 to 10,000:1, or 200:1 to 3,000:1, among others).

Statement 17. The process of any one of statements 5 to 16, wherein the liquid oligomer product comprises any amount of hexenes, octenes, or any combination thereof disclosed herein.

Statement 18. The process of any one of statements 5 to 17, wherein an ethylene trimer has any 1-hexene content disclosed herein (e.g., at least 90 wt. %, 92.5 wt. %, 95 wt. %, 97 wt. %, or 98 wt. % 1-hexene, from 85 wt. % to 99.9 wt. %, from 87.5 wt. % to 99.9 wt. %, from 90 wt. % to 99.9 wt. %, from 92.5 wt. % to 99.9 wt. %, from 95 wt. % to 99.9 wt. %, from 97 wt. % to 99.9 wt. %; or from 98 wt. % to 99.9 wt. % 1-hexene, among others).

Statement 19. The process of any one of statements 5 to 18, wherein an ethylene tetramer has any 1-octene content disclosed herein (e.g., 90 wt. %, 92.5 wt. %, at least 95 wt. %, at least 97 wt. % 1-octene, or 98 wt. % 1-octene, from 90 wt. % to 99.9 wt. %, from 92.5 wt. % to 99.9 wt. %, from 95 wt. % to 99.9 wt. %, from 97 wt. % to 99.9 wt. %, or from 98 wt. % to 99.9 wt. % 1-octene, among others).

Statement 20. The process of any one of statements 5 to 20, wherein the oligomer product has any $C_8/C_6$ ratio disclosed herein (e.g., at least 0.1:1, 0.2:1, 0.3:1, 0.4:1, 0.5:1, 0.7:1 or 1:1 or alternatively, from 0.1:1 to 10:1, from 0.2:1 to 7.5:1, from 0.3:1 to 5:1, 0.3:1 to 4:1, from 0.4:1 to 3:1, from 0.5:1 to 3:1, from 0.7:1 to 3:1, or from 1:1 to 3:1, among others).

Statement 21. The catalyst system of any one of statements 1 to 4, or the process of any one of statements 5 to 20, wherein $L^1$ is a methylene group, an eth-1,2-ylene group, or a prop-1,3-ylene group.

Statement 22. The catalyst system of any one of statements 1 to 4 or 21, or the process of any one of statements 5 to 21, wherein $L^2$ is a methylene group or an eth-1,2-ylene group.

Statement 23. The catalyst system of any one of statements 1 to 4 or 21 to 22, or the process of any one of statements 5 to 22, wherein $R^{11}, R^{12}, R^{13}, R^{14}, R^{15}, R^{16}, R^{17}$, and $R^{18}$ independently is a hydrogen or any $C_1$ to $C_{30}$ organyl group consisting of inert functional groups described herein.

Statement 24. The catalyst system of any one of statements 1 to 4 or 21 to 22, or the process of any one of statements 5 to 22, wherein $R^{11}, R^{12}, R^{13}, R^{14}, R^{15}, R^{16}, R^{17}$, and $R^{18}$ independently are a hydrogen or any $C_1$ to $C_{a0}$ hydrocarbyl group described herein.

Statement 25. The catalyst system of any one of statements 1-4 or 21 to 24, or the process of any one of statements 5 to 24, wherein $R^4$ and $R^5$ independently are a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

Statement 26. The catalyst system of any one of statements 1 to 4 or 21 to 24, or the process of any one of statements 5 to 24, wherein $R^4$ and $R^5$ independently are a $C_1$ to $C_5$ alkyl group, a $C_4$ to $C_{10}$ cycloalkyl group, a phenyl group, or a $C_6$ to $C_{10}$ aryl group.

Statement 27. The catalyst system of any one of statements 1 to 4 or 21 to 24, or the process of any one of statements 5 to 24, where $R^4$ and $R^5$ are combined to form $L^{45}$ forming a ring or ring system including the phosphorus atom where $L^{45}$ is a $C_1$ to $C_{20}$ hydrocarbylene group.

Statement 28. The catalyst system of any one of statements 1 to 4 or 21 to 27, or the process of any one of statements 5 to 27, wherein each X independently is a halide, a carboxylate, or a β-diketonate.

Statement 29. The catalyst system of any one of statements 1 to 4 or 21 to 27, or the process of any one of statements 5 to 27, wherein the chromium salt is a chromium (III) carboxylate, a chromium(III) β-diketonate, or a chromium(III) halide.

Statement 30. The catalyst system of any one of statements 1 to 4 or 21 to 27, or the process of any one of statements 5 to 27, wherein the chromium salt is chromium (III) chloride or chromium(III) acetylacetonate.

Statement 31. The catalyst system of any one of statements 1 to 4 or 28 to 30, or the process of any one of statements 5 to 21 or 28 to 30, wherein the an $N^2$-phosphinyl bicyclic amidine has Structure NPBA 1, NPBA 2, NPBA 3, NPBA 4, or NPBA 5

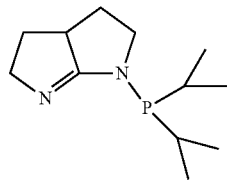

NPBA 1

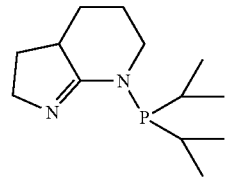 [SMILES: CC(C)P(C(C)C)N1CCCC2CCN=C21]

NPBA 2

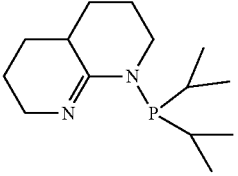

NPBA 3

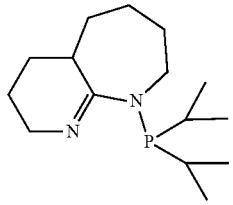

NPBA 4

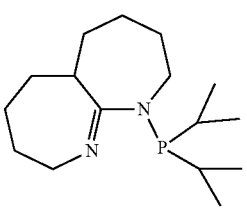

NPBA 5 and the $N^2$-phosphinyl bicyclic amidine chromium salt complex has Structure NPBACr 1, NPBACr 2, NPBACr 3, NPBACr 4, or NPBACr 5

NPBACr 1
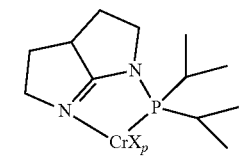

NPBACr 1
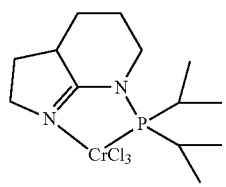

NPBACr 1
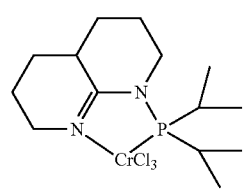

NPBACr 4
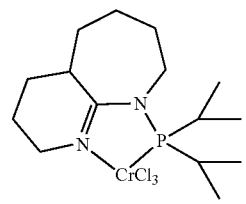

NPBACr 5
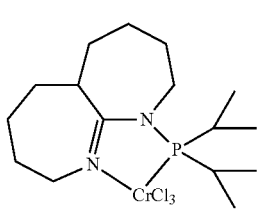

All publications and patents mentioned herein are hereby incorporated in their entirety by reference into the present disclosure. The publications and patents mentioned herein can be utilized for the purpose of describing and disclosing, for example, the constructs and methodologies that are described in the publications, which might be used in connection with the presently described subject matter. The publications discussed throughout the text are provided solely for their disclosure prior to the filing date of the present application. Nothing herein is to be construed as an admission that the inventors are not entitled to antedate such disclosure by virtue of the results of prior investigations, including but not limited to experimental results.

Therefore, the present disclosure is well adapted to attain the ends and advantages mentioned as well as those that are inherent therein. This concludes the detailed description. The particular embodiments disclosed above are illustrative only, as the subject matter of the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the subject matter of the present disclosure. Accordingly, the protection sought herein is as set forth in the claims herein.

What is claimed is:

1. A catalyst system comprising:
   i) (a) an $N^2$-phosphinyl bicyclic amidine chromium salt complex having Structure NPBACr I or Structure NPBACr II NPBACr I
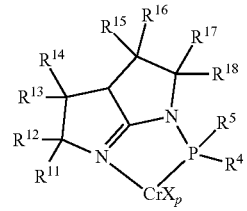

NPBACr II
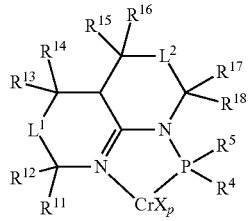

or
(b) a chromium salt and an $N^2$-phosphinyl bicyclic amidine having Structure NPBA I or Structure NPBA II NPBA I
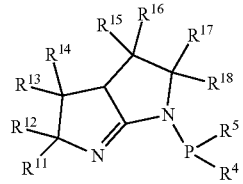

NPBA II
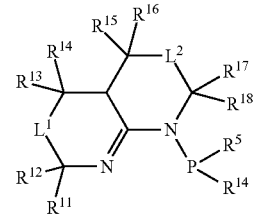

wherein
$R^{11}$, $R^{12}$, $R^{13}$, $R^{14}$, $R^{15}$, $R^{16}$, $R^{17}$, and $R^{18}$ independently are a hydrogen or a $C_1$ to $C_{30}$ organyl group,
$L^1$ and $L^2$ independently are a $C_1$ to $C_{30}$ a hydrocarbylene group,
$R^4$ and $R^5$ independently are a $C_1$ to $C_{30}$ organyl group and $R^4$ and $R^5$ optionally are combined to form $L^{45}$ forming a ring or ring system including the phosphorus atom where $L^{45}$ is a $C_1$ to $C_{30}$ organylene group,
$CrX_p$ is a chromium salt wherein X is a monoanion, and wherein p is an integer from 2 to 6; and
ii) an organoaluminum compound.

2. The catalyst system of claim 1, wherein the chromium salt is a chromium(III) carboxylate, a chromium(III) β-diketonate, or a chromium(III) halide.

3. The catalyst system of claim 1, wherein the chromium salt is chromium(III) chloride or chromium(III) acetylacetonate.

4. The catalyst system of claim 1, wherein the organoaluminum compound comprises an aluminoxane.

5. The catalyst system of claim 4, wherein the aluminoxane comprises methylaluminoxane (MAO), a modified methylaluminoxane, ethylaluminoxane, n-propylaluminoxane, isopropylaluminoxane, n-butylaluminoxane, sec-butylaluminoxane, iso-butylaluminoxane, t-butyl aluminoxane, 1-pentyl-aluminoxane, 2-pentylaluminoxane, 3-pentylaluminoxane, isopentylaluminoxane, neopentylaluminoxane, or mixtures thereof.

6. The catalyst system of claim 1, wherein the catalyst system has an aluminum of the organoaluminum compound to chromium of the chromium salt or chromium of the $N^2$-phosphinyl bicyclic amidine chromium salt complex molar ratio in the range of 10:1 to 5,000:1.

7. The catalyst system of claim 1, wherein $L^1$ and $L^2$ independently are a $C_1$ to $C_{30}$ a methylene group, an eth-1,2-ylene group, or a prop-1,3-ylene group.

8. The catalyst system of claim 1, wherein $R^{11}$, $R^{12}$, $R^{13}$, $R^{14}$, $R^{15}$, $R^{16}$, $R^{17}$, and $R^{18}$ independently are a hydrogen or a $C_1$ to $C_{10}$ hydrocarbyl group.

9. The catalyst system of claim 8, wherein
$R^{11}$, $R^{12}$, $R^{13}$, $R^{14}$, $R^{15}$, $R^{16}$, $R^{17}$, and $R^{18}$ independently are a hydrogen or a $C_1$ to $C_{10}$ hydrocarbyl group,
$L^1$ and $L^2$ independently are a $C_1$ to $C_{30}$ a methylene group, an eth-1,2-ylene group, or a prop-1,3-ylene group,
$R^4$ and $R^5$ independently are a $C_1$ to $C_{10}$ hydrocarbyl group and $R^4$ and $R^5$ optionally are combined to form $L^{45}$ forming a ring or ring system including the phosphorus atom where $L^{45}$ is a $C_1$ to $C_{10}$ hydrocarbyl group,
X is a monoanion, and
wherein p is 3.

10. The catalyst system of claim 1, wherein the $N^2$-phosphinyl bicyclic amidine has Structure NPBA 1, NPBA 2, or NPBA 3

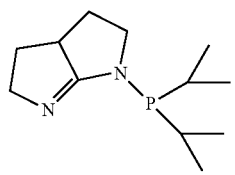

NPBA 1

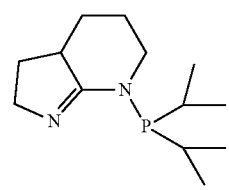

NPBA 1

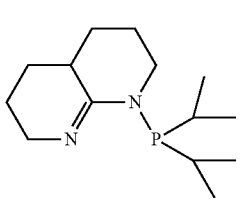

NPBA 1

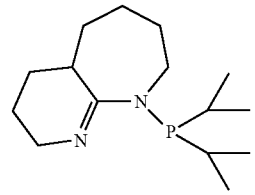

NPBA 4

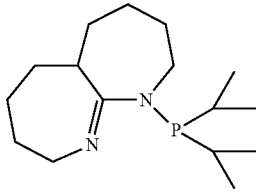

NPBA 5 and the $N^2$-phosphinyl bicyclic amidine chromium salt complex has Structure NPBACr 1, NPBACr 2, or NPBACr 3;

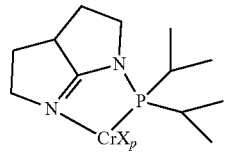

NPBACr 1

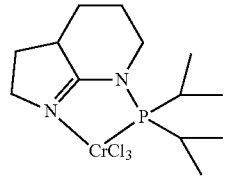

NPBACr 1

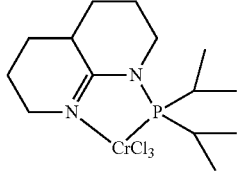

NPBACr 1

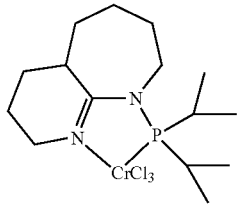

NPBACr 4

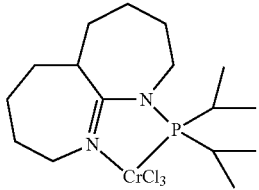

NPBACr 5

11. A process comprising:
a) contacting
   i) ethylene,
   ii) a catalyst system comprising
      (a) (i) an $N^2$-phosphinyl bicyclic amidine chromium salt complex having Structure NPBACr I or Structure NPBACr II

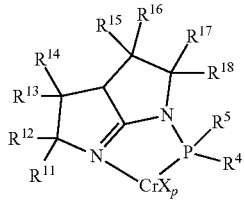

NPBACr I

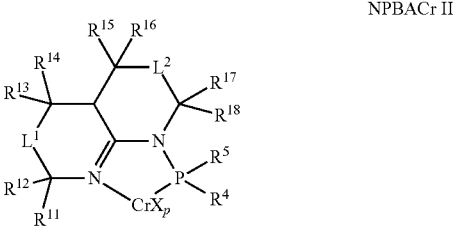

NPBACr II or
      (ii) a chromium salt and an $N^2$-phosphinyl bicyclic amidine having Structure NPBA I or Structure NPBA II

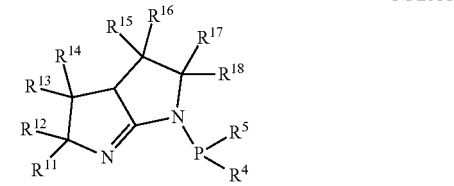

NPBA I

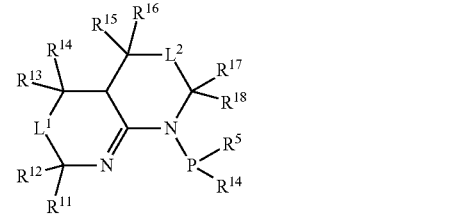

NPBA II wherein
   $R^{11}$, $R^{12}$, $R^{13}$, $R^{14}$, $R^{15}$, $R^{16}$, $R^{17}$, and $R^{18}$ independently are a hydrogen or a $C_1$ to $C_{30}$ organyl group,
   $L^1$ and $L^2$ independently are a $C_1$ to $C_{30}$ a hydrocarbylene group,
   $R^4$ and $R^5$ independently are a $C_1$ to $C_{30}$ organyl group and
   $R^4$ and $R^5$ optionally are combined to form $L^{45}$ forming a ring or ring system including the phosphorus atom where $L^{45}$ is a $C_1$ to $C_{30}$ organylene group,
   $CrX_p$ is a chromium salt wherein X is a monoanion, and wherein p is an integer from 2 to 6,
      (b) an organoaluminum compound, and
   iii) optionally an organic reaction medium; and
b) forming an oligomer product in a reaction zone.

12. The process of claim 11, wherein the chromium salt is a chromium(III) carboxylate, a chromium(III) β-diketonate, or a chromium(III) halide.

13. The process of claim 11, wherein the chromium salt is chromium(III) chloride or chromium(III) acetylacetonate.

14. The process of claim 11, wherein the organoaluminum compound comprises an aluminoxane comprising methylaluminoxane (MAO), a modified methylaluminoxane, ethylaluminoxane, n-propylaluminoxane, isopropylaluminoxane, n-butylaluminoxane, sec-butylaluminoxane, isobutylaluminoxane, t-butyl aluminoxane, 1-pentylaluminoxane, 2-pentylaluminoxane, 3-pentyl-aluminoxane, isopentylaluminoxane, neopentylaluminoxane, or mixtures thereof.

15. The process of claim 11, wherein the reaction zone has an aluminum of the organoaluminum compound to chromium of the chromium salt or chromium of the $N^2$-phosphinyl bicyclic amidine chromium salt complex molar ratio in the range of 10:1 to 5,000:1.

16. The process of claim 11, wherein
   $R^{11}$, $R^{12}$, $R^{13}$, $R^{14}$, $R^{15}$, $R^{16}$, $R^{17}$, and $R^{18}$ independently are a hydrogen or a $C_1$ to $C_{10}$ hydrocarbyl group,
   $L^1$ and $L^2$ independently are a $C_1$ to $C_{30}$ a methylene group, an eth-1,2-ylene group, or a prop-1,3-ylene group,
   $R^4$ and $R^5$ independently are a $C_1$ to $C_{10}$ hydrocarbyl group and $R^4$ and $R^5$ optionally are combined to form $L^{45}$ forming a ring or ring system including the phosphorus atom where $L^{45}$ is a $C_1$ to $C_{10}$ hydrocarbyl group,
   X is a monoanion, and
   wherein p is 3.

17. The process of claim 11, wherein the $N^2$-phosphinyl bicyclic amidine has Structure NPBA 1, NPBA 2, or NPBA 3

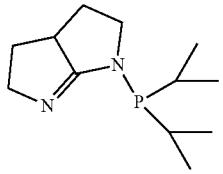

NBPA 1

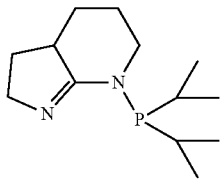

NBPA 1

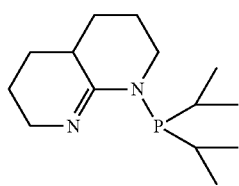 [SMILES: CC(C)P(C(C)C)N1CCCC2CCCN=C21]

NBPA 1

NBPA 4

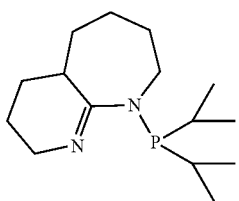

NBPA 5

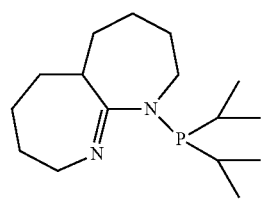

and the N²-phosphinyl bicyclic amidine chromium salt complex has Structure NPBACr 1, NPBACr 2, or NPBACr 3

NPBACr 1

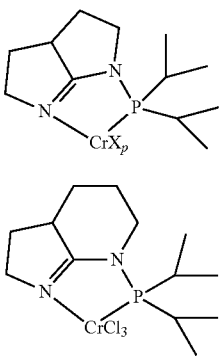

NPBACr 1

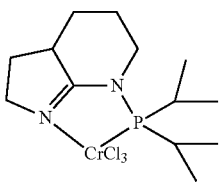

NPBACr 1

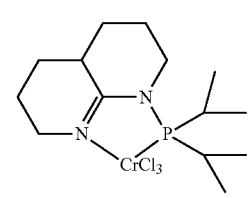

NPBACr 4

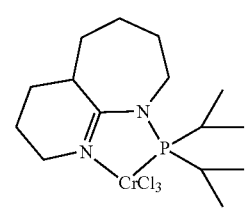

NPBACr 5

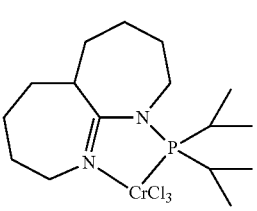

18. The process of claim 11, wherein an ethylene trimer has a 1-hexene content of at least 95 wt. % and/or an ethylene tetramer has a 1-octene content of at least 95 wt. %.

19. The process of claim 11, wherein the oligomer product has a $C_8/C_6$ ratio is at least 1.5:1.

* * * * *